US007960357B2

(12) United States Patent
Dirks et al.

(10) Patent No.: US 7,960,357 B2
(45) Date of Patent: *Jun. 14, 2011

(54) PKR ACTIVATION VIA HYBRIDIZATION CHAIN REACTION

(75) Inventors: Robert Dirks, Long Island City, NY (US); Niles A. Pierce, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/544,306

(22) Filed: Oct. 6, 2006

(65) Prior Publication Data

US 2007/0087334 A1     Apr. 19, 2007

Related U.S. Application Data

(60) Provisional application No. 60/725,011, filed on Oct. 7, 2005.

(51) Int. Cl.
*A61K 48/00* (2006.01)
*C07H 21/04* (2006.01)
(52) U.S. Cl. ............ 514/44; 536/23.3; 536/24.31; 435/6
(58) Field of Classification Search .................. None
See application file for complete search history.

(56) References Cited

U.S. PATENT DOCUMENTS

| | | | |
|---|---|---|---|
| 4,714,680 A | 12/1987 | Civin | |
| 4,897,355 A | 1/1990 | Eppstein et al. | |
| 4,965,204 A | 10/1990 | Civin | |
| 5,057,410 A | 10/1991 | Kawasaki et al. | |
| 5,061,620 A | 10/1991 | Tsukamoto et al. | |
| 5,459,127 A | 10/1995 | Felgner et al. | |
| 5,579,793 A | 12/1996 | Gajewski et al. | |
| 5,643,741 A | 7/1997 | Tsukamoto et al. | |
| 5,677,136 A | 10/1997 | Simmons et al. | |
| 5,716,827 A | 2/1998 | Tsukamoto et al. | |
| 5,750,397 A | 5/1998 | Tsukamoto et al. | |
| 5,928,913 A | 7/1999 | Efstathiou et al. | |
| 5,989,823 A | 11/1999 | Jayasena et al. | |
| 6,242,246 B1 | 6/2001 | Gold et al. | |
| 6,261,783 B1 | 7/2001 | Jayasena et al. | |
| 6,361,944 B1 | 3/2002 | Mirkin et al. | |
| 6,361,945 B1 * | 3/2002 | Becker et al. | 435/6 |
| 6,485,965 B1 | 11/2002 | Klatzmann et al. | |
| 6,506,559 B1 | 1/2003 | Fire et al. | |
| 6,555,367 B1 | 4/2003 | Spence et al. | |
| 6,899,871 B2 | 5/2005 | Kasahara et al. | |
| 7,033,834 B2 | 4/2006 | Valerio et al. | |
| 2002/0051769 A1 | 5/2002 | Zhang | |
| 2002/0172950 A1 | 11/2002 | Kenny et al. | |
| 2003/0092162 A1 | 5/2003 | Shankara et al. | |
| 2004/0223953 A1 | 11/2004 | Kung et al. | |
| 2005/0260635 A1 | 11/2005 | Dirks et al. | |
| 2006/0228733 A1 | 10/2006 | Pierce et al. | |
| 2006/0234261 A1 | 10/2006 | Pierce et al. | |
| 2009/0011956 A1 | 1/2009 | Yin et al. | |

FOREIGN PATENT DOCUMENTS

| | | |
|---|---|---|
| EP | 0273085 | 7/1988 |
| WO | WO 94/01550 | * 1/1994 |
| WO | WO 99/31276 | * 6/1999 |
| WO | WO 2007/008276 | 1/2007 |

OTHER PUBLICATIONS

Sokol et al (Proc. Nat. Acad. Sci. USA 95: 11538-11543, 1998).*
Judge et al (Human Gene Therapy 19: 111-124, 2008).*
Pouton et al (Adv. Drug Del. Rev. 46: 187-203, 2001).*
Opalinska et al (Nature Reviews Drug Discovery, 2002, vol. 1, pp. 503-514).*
Caplen (Expert Opin. Biol. Ther. 2003, vol. 3, pp. 575-586, 2003).*
Coburn et al. (Journal of Antimicrobial Chemotherapy. vol. 51, pp. 753-756, 2003).*
Check (Nature, 2003, vol. 425, pp. 10-12).*
Zhang et al (Current Pharmaceutical Biotechnology 2004, vol. 5, pp. 1-7).*
Read et al (Adv. Gen. 53:19-46, 2005).*
Copelli et al (Curr. Pharm. Des. 11: 2825-2840, 2005).*
Zhou et al (Curr. Top. Med. Chem. 6:901-911, 2006).*
Kokaiwado et al (IDrugs 11(4): 274-278, 2008).*
Nutiu and Li (J. Am. Chem. Soc. 125(16): 4771-4778, 2003).*
Williams et al (Oncogene 18: 6112-6120, 1999).*
Ladiges et al (Mech. Ageing Dev. 114: 123-132, 2000).*
Mittlestadt et al (Nucl. Acids Res. 36(3): 998-1008, 2008).*
Amarzguioui et al., "Rational design and in vitro and in vitro delivery of Dicer substrate siRNA,", Nature Protocols, vol. 1, No. 2, pp. 508-517, 2006.
Bois et al., "Topological constraints in nucleic acid hybridization kinetics," Nucleic Acids Research, vol. 33, No. 13, pp. 4090-4095, 2005.
Definition for "substantial" from Merriam-Webster Online Dictionary. Downloaded from Merriam-Webster.com on Mar. 5, 2008.
Dohjima, T. et al., "Small Interfering RNAs Expressed from a Pol III Promoter Suppress the EWS/Fli-1 Transcript in an Ewing Sarcoma Cell Line", Molecular Therapy, vol. 7, No. 6, pp. 811-816, Jun. 2003.
Elbashir et al., "Functional anatomy of siRNAs for mediating efficient RNAi in Drosophila melanogaster embryo lysate", The EMBO Journal, vol. 20, No. 23, pp. 6877-6888, 2001.
Fire et al., "Potent and specific genetic interference by double-stranded RNA in Caenorhabditis elegans", Nature, vol. 391, pp. 806-811, Feb. 19, 1998.
Jhaveri et al., "In vitro selection of signaling aptamers", Nature Biotechnology, vol. 18, pp. 1293-1297, Dec. 2000.
Kim et al., "Synthetic dsRNA Dicer substrates enhance RNAi potency and efficacy", Nature Biotechnology, vol. 23, No. 2, pp. 222-226, Feb. 2005.
Mahato et al., "Modulation of gene expression by antisense and antigene oligodeoxynucleotides and small interfering RNA", Expert Opin. Drug Deliv., vol. 2, No. 1, pp. 3-28. 2005.

(Continued)

*Primary Examiner* — Richard Schnizer
(74) *Attorney, Agent, or Firm* — Knobbe, Martens, Olson & Bear, LLP

(57) ABSTRACT

The present application relates to the use of hybridization chain reaction (HCR) to form double stranded RNA polymers in the presence of a target, such as a nucleic acid associated with a disease or disorder. The RNA polymers are preferably able to activate the RNA-dependent kinase PKR. Activation of PKR via RNA-HCR can be used to treat a wide variety of diseases and disorders by specifically targeting diseased cells.

34 Claims, 9 Drawing Sheets

OTHER PUBLICATIONS

Park et al., "Rapid Identification of *Candida dubliniensis* Using a Species-Specific Molecular Beacon", Journal of Clinical Microbiology, vol. 38, No. 8, pp. 2829-2836, 2000.

Scherer et al., "Approaches for the sequence-specific knockdown of mRNA", Nature Biotechnology, vol. 21, No. 12, pp. 1457-1465, 2003.

Seelig et al., "Catalyzed Relaxation of a Metastable DNA Fuel", Journal American Chemical Society, vol. 128, No. 37, pp. 12211-12220, 2006.

Tijsterman et al., "Dicers at RISC: The Mechanism of RNAi", Cell, vol. 117, pp. 1-3, 2004.

Vermeulen et al., "The contributions of dsRNA structure to Dicer specificity and efficiency", RNA, vol. 11, pp. 674-682, 2005.

Yin et al., "Programming biomolecular self-assembly pathways", Nature, vol. 451, pp. 318-323, Jan. 17, 2008.

International Search Report and Written Opinion from PCT/US2005/009471, dated Mar. 8, 2006.

Supplementary European Search Report from PCT/US2005/009471, dated May 6, 2008.

U.S. File History printed Jun. 16, 2009 for U.S. Appl. No. 11/087,937, filed Mar. 22, 2005, entitled "Hybridization Chain Reaction,".

U.S. File History printed Jun. 16, 2009 for U.S. Appl. No. 11/371,347, filed Mar. 7, 2006, entitled "Colorimetric Readout of Hybridization Chain Reaction,".

U.S. File History printed Jun. 16, 2009 for U.S. Appl. No. 11/371,346, filed Mar. 7, 2006, entitled "Hybridization Chain Reaction Amplification for in Situ Imaging,".

U.S. File History printed Jun. 16, 2009 for U.S. Appl. No. 12/040,735, filed Feb. 29, 2008, entitled "Triggered RNAi,".

U.S. File History printed Jun. 16, 2009 for U.S. Appl. No. 12/152,893, filed May 16, 2008, entitled "A Versatile Nucleic Acid Hairpin Motif for Programming Biomolecular Self-Assembly Pathways,".

Flamm et al., "RNA folding at elementary step resolution," RNA, vol. 6, pp. 325-338, 2000.

Coleman, R.S. and Pires, R.M. Covalent cross-linking of duplex DNA using 4-thio-2'-deoxyuridine as a readily modifiable platform for introduction of reactive functionality into oligonucleotides. Nucleic Acids Research, 1997. 25: p. 4771-4777.

Higuchi et al. Selective regulation of mutant K-ras mRNA expression by photo-cross-linking antisense oligonucleotide. Nucleic Acids Symposium Series (2007) vol. 51 (1) pp. 443-444.

International Search Report and Written Opinion from PCT/US2008/055559, dated Sep. 3, 2008.

Killops, K.L., Campos, L.M., Hawker, C.J. Robust, Efficient, and Orthogonal Synthesis of Dendrimers via Thiol-ene "Click" Chemistry. Journal of the American Chemical Society, 2008. 130: p. 5062-5064.

Pieles, U. and Englisch, U. Psoralen covalently linked to oligodeoxyribonucleotides: synthesis, sequence specific recognition of DNA and photo-cross-linking to purimidine residues of DNA. Nucleic Acids Research, 1989. 17: p. 285-299.

Qian, X., L. Jin, and R.V. Lloyd, In situ hybridization: basic approaches and recent development. The Journal of Histotechnology, 2004. 27(1): p. 53-67.

Willis, M.C., et al. Photocross-linking of 5-Iodouracil-Substituted RNA and DNA to Proteins. Science, 1993. 262: p. 1255-1257.

Office Action dated Feb. 4, 2010 in U.S. Appl. No. 12/152,893.
Office Action dated Apr. 1, 2010 in U.S. Appl. No. 12/467,755.
Office Action dated Apr. 16, 2010 in U.S. Appl. No. 12/454,799.
Final Office Action dated Sep. 20, 2010 for U.S. Appl. No. 12/454,799.
Final Office Action dated Sep. 17, 2010 for U.S. Appl. No. 12/467,755.
Final Office Action dated Oct. 15, 2010 for U.S. Appl. No. 12/152,893.
Office Action dated Nov. 9, 2010 for U.S. Appl. No. 12/040,735.

Garcia, et al., "Impact of Protein Kinase PKR in Cell Biology: from Antiviral to Antiproliferative Action." Microbiology and Molecular Biology Reviews vol. 70, No. 4 (Dec. 2006): pp. 1032-1060.

Manche, et al., "Interactions between Double-Stranded RNA Regulators and the Protein Kinase DAI." Molecular and Cellular Biology, vol. 12, No. 11 (Nov. 1992): pp. 5238-5248.

Venkataraman, et al., "Selective cell death mediated by small conditional RNAs." PNAS, vol. 107, No. 39 (Sep. 28, 2010): pp. 16777-16782.

Zheng, et al., "Activation of the protein kinase PKR by short double-stranded RNAs with single-stranded tails." RNA, vol. 10, No. 12 (2004): pp. 1934-1945.

Caltech News Release, "Caltech Scientists Create New Process to Program", Sep. 6, 2010.

National Science Foundation, "These Cells Will Self-Destruct in Five . . . Four . . . ", Press Release 10-160, p. 1-3, 2010 (RS Jan. 18, 2011).

Schipani, Vanessa, "A targeted cancer therapy?" The Scientist, Sep. 7, 2010 blog post, http://www.the-scientist.com/blog/display/57674/.

The Naked Scientists: Science Radio & Science Podcasts, "RNA-away cancer cells", Sep. 12, 2010, http://www.thenakedscientists.com/HTML/content/news/news/2051/.

Venkataraman et al. "Selective Cell Death Mediated by Small Conditional RNAs", Proc Natl Acad Sci USA, early edition, approved Jul. 21, 2010, p. 1-6.

Venkataraman et al. Abstract of "Selective Cell Death Mediated By Small Conditional RNAs", Proc Natl Acad Sci USA, early edition, http://www.pnas.org/content/early/2010/09/01/1006377107.abstract.

Bushnell et al., "ProbeDesigner: for the design of probesets for branched DNA (bDNA) signal amplification assays," Bioinformatics, 15(5):348-355, 1999.

Collins et al., "A branched DNA signal amplification assay for quantification of nucleic acid targets below 100 molecules/ml," Nucleic Acids Res, 25(15):2979-2984, 1997.

van de Corput et al., "Sensitive mRNA Detection by Fluorescence In Situ Hybridization Using Horseradish Peroxidase-labeled Oligodeoxynucleotides and Tyramide Signal Amplification," J. Histochem Cytochem, 46(11):1249-1259, 1998.

Dirks et al., "Paradigms for computational nucleic acid design," *Nucleic Acids Research*, 2004, pp. 1392-1403, vol. 32, No. 4, Oxford University Press 2004.

Dirks et al., "Triggered amplification by hybridization chain reaction," *PNAS*, Oct. 26, 2004, pp. 15275-15278, vol. 101, No. 43.

Dohjima, T. et al. 2003. Small Interfering RNAs Expressed from a Pol III Promoter Suppress the EWS/Fli-1 Transcript in an Ewing Sarcoma Cell Line. Molecular Therapy 7: 811-816.

Elghanian et al., "Selective colorimetric detection of polynucleotides based on the distance-dependent optical properties of gold nanoparticles," Science, 277(5329):1078-1081,1997.

Ellington et al., "In vitro selection of RNA molecules that bind specific ligands," Nature 346:818-822, 1990.

Felgner, et al. 1997. Nomenclature for synthetic gene delivery systems. Hum Gene Ther 8:511-512.

Ferkol, et al. 1993. Gene transfer into the airway epithelium of animals by targeting the polymeric immunoglobulin receptor. J. Clin Invest 92(5):2394-2400.

Ferkol, et al. 1993. Regulation of the phosphoenolpyruvate carboxykinase/human factor IX gene introduced into the livers of adult rats by receptor-mediated gene transfer. FASEB J 7:1081-1091.

Flamm et al., "RNA folding at elementary step resolution," *RNA*, 2000, pp. 325-338, vol. 6, Cambridge University Press.

Friedrich, et al. 2004. RNA molecules as anti-cancer agents. Seminars in Cancer Biology 14:223-230.

Friedrich, et al. 2005. A Cellular Screening Assay to Test the Ability of PKR to Induce Cell Death in Mammalian Cells. Molecular Therapy 12:969-975.

Heidel, J.D. 2005. Targeted, systematic non-viral delivery of small interfering RNA in vivo. Doctoral thesis, California Institute of Technology. 128p.

Hofacker et al., "Fast folding and comparison of RNA secondary structures," *Monatshefte für Chemie*, 1994, pp. 167-188, vol. 125.

Hughes et al., "Double Labeling wit Fluorescence In Situ Hybridization in *Drosophila* Whole-Mount Embryos," *Bio Techniques*, 24(4):530-532, 1998.

Huizenga et al., "A DNA Aptamer That Binds Adenosine and ATP." Biochemistry 34:656-665 (1995.

Iqbal et al., "A review of molecular recognition technologies for detection of biological threat agents", Biosensors & Bioelectronics, 2000, pp. 549-578, vol. 15.

Jagus, et al. 1999. PKR, apoptosis and cancer. The International Journal of Biochemistry 31:123-138.

Kislauskis et al. "Isoform-specific 3'-untranslated Sequences Sort α-cardiac and β-cytoplasmic Actin Mesenger RNAs to Different ytoplasmic Compartments," The Journal of Cell Biology, 123(1):165 172, 1993.

Kosman, et al., "Multiplex Detection of RNA Expression in *Drosophila* Embryos," Science, 305:846, 2004.

Lawrence et al., "Highly Localized Tracks of Specific Transcripts within Interphase Nuclei Visualized by In Situ Hybridication," Cell, 57:493-502, 1989.

Levsky et al., "Single-Cell Gene Expression Profiling," Science 297:836-840,2002.

Liu et al., "A colorimetric lead biosensor using DNAzyme-directed assembly of gold nanoparticles," J. Am. Chem. Soc., 125(22):6642-6643, 2003.

Macechko et al., "Comparison of Immunologic Amplification vs Enzymatic Deposition of Fluorochrome-conjugated Tyramide as Detection Systems for FISH," J Histochem Cytochem, 45(3):359-363, 1997.

Manche et al. 1999. Interactions between double-stranded RNA regulators and the protein kinase DAI. Molecular and Cellular Biology 12:5238-5248.

Matsui, T. et al. 2001. Expression of unphosphorylated form of human double-stranded RNA-activated protein kinase in *Escherichia coli*. Biochem Biophys Res Comm 284:798-807.

Nakano et al., "Selection for thermodynamically stable DNA tetraloops using temperature gradient gel electrophoresis reveals four motifs: d(cGNNAg), d(cGNABg), d(cCNNGg), and d(gCNNGc)," *Biochemistry*, 2002, pp. 14281-14292, vol. 41, American Chemical Society.

Nutiu et al., "Structure-switching signaling aptamers," *J. Am. Chem. Soc.*, 2003, pp. 4771-4778, vol. 125, American Chemical Society.

Perales, et al. 1994. Gene Transfer in vivo: Sustained Expression and Regulation of Genes Introduced into the Liver by Receptor-Targeted Uptake. Proc Nat Acad Sci 91:4086-4090.

Player et al., "Single-copy Gene Detection Using Branched DNA (bDNA)) In Situ Hybridization," J. Histochem & Cytochem, 49(5):603-611, 2001.

Qian et al., "Recent Developments in Signal Amplification Methods for In Situ Hybridization," Diagnostic Molecular Pathology, 12(1):1-13, 2003.

Rachofsky et al., "Probing structure and dynamics of DNA with 2-aminopurine: Effects of local environment on fluorescence," *Biochemistry*, 2001, pp. 946-956, vol. 40.

Schwartz, et al. 1990. Cloning and functional analysis of multiply spliced mRNA species of human immunodeficiency virus type 1. J. Virol. 1990; 64(6): 2519-2529.

Schweitzer et al., "Combining nucleic acid amplification and detection," Curr Opin Biotechnol, 12:21-27, 2001.

Seeman, "Nucleic acid junctions and lattices," *J. Theor. Biol.*, 1982, pp. 237-247, vol. 99, Academic Press Inc. (London) Ltd.

Shir, et al., 2002. Inhibition of glioma growth by tumor-specific activation of double-stranded RNA—dependent protein kinase PKR. Nature Biotechnology 20:895-900.

Storhoff et al., "One-pot colorimetric differentiation of polynucleotides with single base imperfections using gold nanoparticles," J. Am. Chem. Soc., 120:1959-1964, 1998.

Tuerk et al., "Systematic Evolution of Ligands by Exponential Enrichment: RNA Ligands to Bacteriophage T4 DNA Polymerase," Science 249:505-510, 1990.

Tyagi et al., "Molecular Beacons: Probes that Fluoresce upon Hybridization," Nature Biotechnology 14:303-308, 1996.

Wagner, et al. 1990. Transferrin-Polycation Conjugates as Carriers for DNA Uptake into Cells. Proc Natl Acad Sci USA 87(9):3410-3414.

Wilkie et al., "Transcribed genes are localized according to chromosomal position within polarized *Drosophila* embryonic nuclei," Current Biology, 9: 1263-1266, 1999.

Williams, B.R.G. 1999. PKR; a sentinel kinase for cellular stress. Oncogene 18:6112-6120.

Wu, et al., 1997. A Model for the Double-stranded RNA (dsRNA)-dependent Dimerization and Activation of the dsRNA-activated Protein Kinase PKR. The Journal of Biological Chemistry 272:1291-1296.

Wu, et al., 1987. Receptor-mediated in vitro gene transformation by a soluble DNA carrier system. J Biol Chem 262(10):4429-4432.

Zheng, et al., 2004. Activation of the Protein Kinase PKR by Short Double-stranded RNAs with Single-stranded Tails. RNA 10:1934-1945.

Zuker et al., "Optimal computer folding of large RNA sequence using thermodynamics and auxiliary information," Nucleic Acids Research, vol. 9, No. 1, pp. 133-147 (1981).

"The Handbook—A Guide to Fluorescent Probes and Labeling Technologies,"10th Ed. (available at http://www.probes.com), 2005 (RS Jan. 18, 2011).

Tuberfiled, et al., "DNA fuel for free-running nanomachines," Physical Review Letters, vol. 90, No. 11, pp. 118102-1-118102-4, (Mar. 21, 2003).

Völker, et al., "Conformational energetics of stable and metastable states formed by DNA triplet repeat oligonucleotides: implications for triplet expansion diseases," PNAS, vol. 99, No. 23, pp. 14700-14705, (Nov. 12, 2002).

Extended European Search Report dated Apr. 22, 2010 in European Patent Application No. 06836249.0.

* cited by examiner

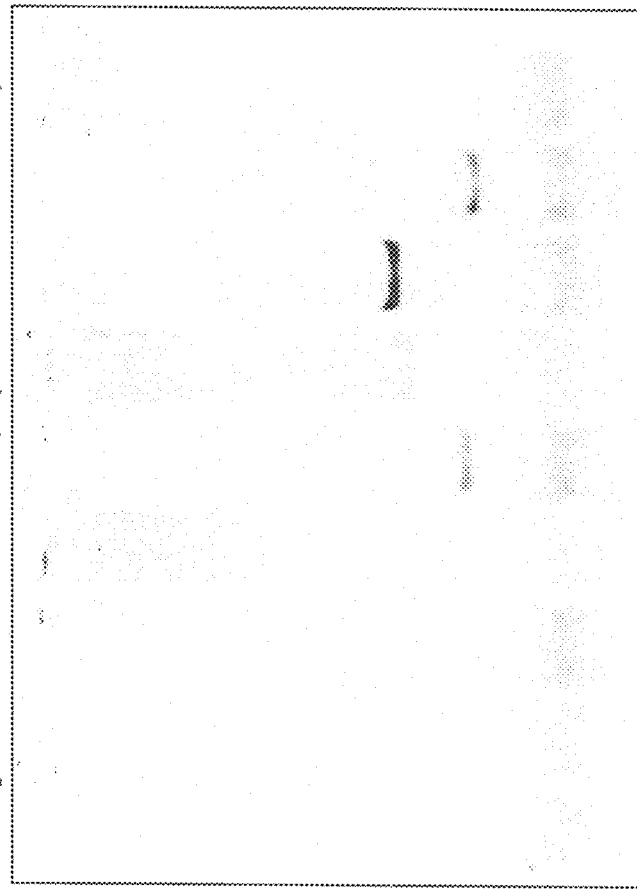
FIG. 6A Ewing's sarcoma RNA-HCR polymer formation study

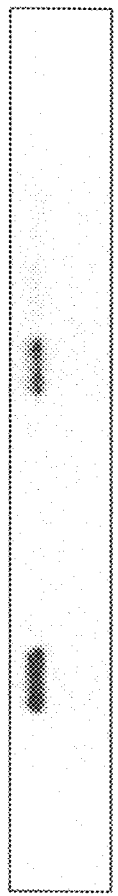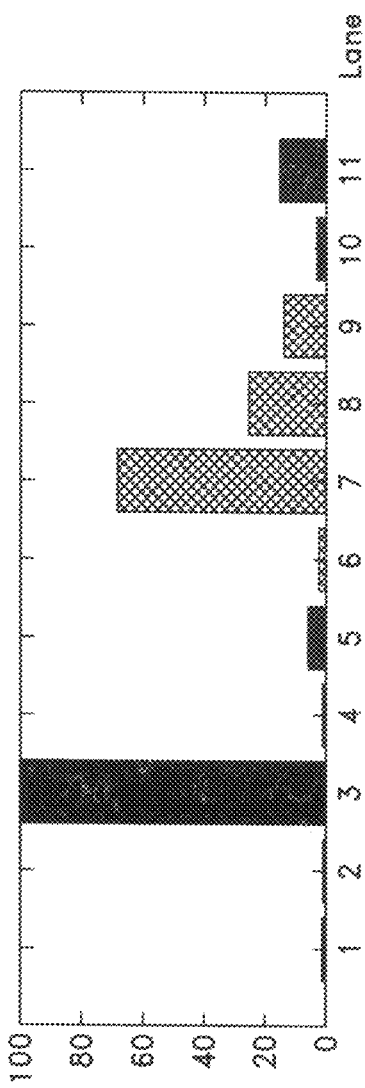
FIG. 7A

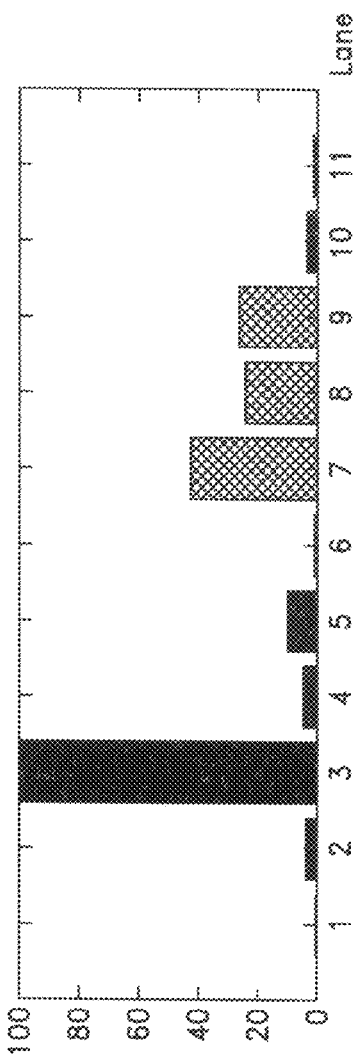
FIG. 7B

SEQUENCE LISTING

<160> NUMBER OF SEQ ID NOS: 16

<210> SEQ ID NO 1

-continued

```
<211> LENGTH: 18
<212> TYPE: RNA
<213> ORGANISM: Artificial Sequence
<220> FEATURE:
<223> OTHER INFORMATION: Synthetic RNA sequence encoding fusion
      mutation for Ewing's sarcoma without flanking regions

<400> SEQUENCE: 1
agcagaaccc uucuuaug                                                       18

<210> SEQ ID NO 2
<211> LENGTH: 36
<212> TYPE: RNA
<213> ORGANISM: Artificial Sequence
<220> FEATURE:
<223> OTHER INFORMATION: Synthetic RNA hairpin monomer sequence

<400> SEQUENCE: 2
cagacauaag aagguucag cagaacccuu cuuaug                                    36

<210> SEQ ID NO 3
<211> LENGTH: 36
<212> TYPE: RNA
<213> ORGANISM: Artificial Sequence
<220> FEATURE:
<223> OTHER INFORMATION: Synthetic RNA hairpin monomer sequence

<400> SEQUENCE: 3
gaacccuucu uaugucugca uaagaagggu ucugcu                                   36

<210> SEQ ID NO 4
<211> LENGTH: 50
<212> TYPE: RNA
<213> ORGANISM: Artificial Sequence
<220> FEATURE:
<223> OTHER INFORMATION: Synthetic RNA sequence encoding fusion
      mutation for Ewing's sarcoma with flanking regions

<400> SEQUENCE: 4
cagagcagca gcuacgggca gcagaacccu ucuuaugacu cagucagaag                    50

<210> SEQ ID NO 5
<211> LENGTH: 50
<212> TYPE: RNA
<213> ORGANISM: Artificial Sequence
<220> FEATURE:
<223> OTHER INFORMATION: Synthetic RNA sequence encoding non-mutant
      mRNA sequence

<400> SEQUENCE: 5
auauagccaa cagagcagca gcuacgggca gcagaguuca uuccuuccga                    50

<210> SEQ ID NO 6
<211> LENGTH: 50
<212> TYPE: RNA
<213> ORGANISM: Artificial Sequence
<220> FEATURE:
<223> OTHER INFORMATION: Synthetic RNA sequence encoding non-mutant
      mRNA sequence

<400> SEQUENCE: 6
ugagugucaa agaagacccu ucuuaugacu cagucagaag aggagcuugg                    50

<210> SEQ ID NO 7
<211> LENGTH: 13
<212> TYPE: DNA
<213> ORGANISM: Artificial Sequence
<220> FEATURE:
```

```
<223> OTHER INFORMATION: Synthetic helper DNA sequence

<400> SEQUENCE: 7
cttctgactg agt                                                          13

<210> SEQ ID NO 8
<211> LENGTH: 19
<212> TYPE: DNA
<213> ORGANISM: Artificial Sequence
<220> FEATURE:
<223> OTHER INFORMATION: Synthetic helper DNA sequence

<400> SEQUENCE: 8
gcccgtagct gctgctctg                                                    19

<210> SEQ ID NO 9
<211> LENGTH: 18
<212> TYPE: RNA
<213> ORGANISM: Artificial Sequence
<220> FEATURE:
<223> OTHER INFORMATION: Synthetic RNA sequence encoding fusion
      mutation for glioma without flanking regions

<400> SEQUENCE: 9
aaaagaaagg uaauuaug                                                     18

<210> SEQ ID NO 10
<211> LENGTH: 36
<212> TYPE: RNA
<213> ORGANISM: Artificial Sequence
<220> FEATURE:
<223> OTHER INFORMATION: Synthetic RNA hairpin monomer sequence

<400> SEQUENCE: 10
cauaauuacc uuucuuuugg gcaaaagaaa gguaau                                 36

<210> SEQ ID NO 11
<211> LENGTH: 36
<212> TYPE: RNA
<213> ORGANISM: Artificial Sequence
<220> FEATURE:
<223> OTHER INFORMATION: Synthetic RNA hairpin monomer sequence

<400> SEQUENCE: 11
aaaagaaagg uaauuaugau uaccuuucuu uugccc                                 36

<210> SEQ ID NO 12
<211> LENGTH: 50
<212> TYPE: RNA
<213> ORGANISM: Artificial Sequence
<220> FEATURE:
<223> OTHER INFORMATION: Synthetic RNA sequence encoding fusion
      mutation for glioma with flanking regions

<400> SEQUENCE: 12
agucgggcuc uggaggaaaa gaaagguaau uaugugguga cagaucacgg                  50

<210> SEQ ID NO 13
<211> LENGTH: 50
<212> TYPE: RNA
<213> ORGANISM: Artificial Sequence
<220> FEATURE:
<223> OTHER INFORMATION: Synthetic RNA sequence encoding non-mutant
      mRNA sequence

<400> SEQUENCE: 13
cugcccggcg agucgggcuc uggaggaaaa gaaaguuugc caaggcacga                  50
```

```
<210> SEQ ID NO 14
<211> LENGTH: 50
<212> TYPE: RNA
<213> ORGANISM: Artificial Sequence
<220> FEATURE:
<223> OTHER INFORMATION: Synthetic RNA sequence encoding non-mutant
      mRNA sequence

<400> SEQUENCE: 14
ugaagaagug uccccguaau uaugugguga cagaucacgg cucgugcguc                50

<210> SEQ ID NO 15
<211> LENGTH: 16
<212> TYPE: DNA
<213> ORGANISM: Artificial Sequence
<220> FEATURE:
<223> OTHER INFORMATION: Synthetic helper DNA sequence

<400> SEQUENCE: 15
ccgtgatctg tcacca                                                    16

<210> SEQ ID NO 16
<211> LENGTH: 16
<212> TYPE: DNA
<213> ORGANISM: Artificial Sequence
<220> FEATURE:
<223> OTHER INFORMATION: Synthetic helper DNA sequence

<400> SEQUENCE: 16
cctccagagc ccgact                                                    16
```

PKR ACTIVATION VIA HYBRIDIZATION CHAIN REACTION

CROSS-REFERENCE TO RELATED APPLICATIONS

The present application claims priority to U.S. Provisional Application No. 60/725,011, filed Oct. 7, 2005, which is hereby incorporated by reference in its entirety.

BACKGROUND OF THE INVENTION

1. Field of the Invention

The present application relates generally to the use of hybridization chain reaction to create RNA polymers that are able to activate the RNA-dependent kinase PKR.

2. Description of the Related Art

Hybridization Chain Reaction (HCR) is a method for the triggered hybridization of nucleic acid molecules, typically starting from metastable, monomer hairpins. HCR is described, for example, in U.S. patent application Ser. No. 11/087,937, filed Mar. 22, 2005 (published as U.S. Publication No. 2005-0260635 on Nov. 24, 2005), and Dirks and Pierce (Dirks, R. and N. Pierce, Proc. Natl. Acad. Sci. USA 101(43): 15275-15278 (2004)), which are incorporated herein by reference in their entirety. In a simple version of this process, metastable monomer hairpins undergo a chain reaction of hybridization events to form a nicked helix when triggered by a nucleic acid initiator strand. A fundamental principle behind HCR is that short loops are resistant to invasion by complementary single-stranded nucleic acids. This stability allows for the storage of potential energy in the form of loops; potential energy is released when a triggered conformational change allows the single-stranded bases in the loops to hybridize with a complementary strand. One embodiment of HCR is illustrated in FIG. 1.

HCR can be used for a wide variety of purposes, for example, to create a visual signal that identifies the presence of one or more target analytes in a sample using nano-gold particles, as described by U.S. patent application Ser. No. 11/371,347, filed on Mar. 7, 2006, herein incorporated by reference. It can also be used for in situ imaging and detection applications, as described by U.S. patent application Ser. No. 11/371,346, filed on Mar. 7, 2006, herein incorporated by reference. As described in detail below, it has now been found that HCR can be used to create RNA polymers in target cells, thereby activating the protein kinase PKR.

Protein kinases and other cell-signaling messengers are activated during an immune response. In vitro studies show that PKR is activated when two PKR molecules dimerize and phosphorylate each other in complex with RNA duplexes longer than approximately 30 bp, and that the strength of the activation increases with duplex length up to ~85 bp (Manche, L. et al. *Molecular and Cellular Biology* 12:5238-5248 (1992); Wu, S., and R. J. Kaufman. *The Journal of Biological Chemistry* 272:1291-1296 (1997); which are incorporated herein by reference in their entirety). Activation of PKR can lead to selective cell death, which is a strategy envisioned for the development of therapies for cancer (Shir, A. and A. Levitski. *Nature Biotechnology* 20:895-900 (2002); Friedrich, I. et al. *Serminars in Cancer Biology* 14:223-230 (2004); Friedrich, I. et al. *Molecular Therapy* 12:969-975 (2005); which are incorporated herein by reference in their entirety). Exploiting these activation properties, it was demonstrated that binding of anti-sense RNA to a region that spans the splice point of an oncogenic mRNA fusion entity resulted in creation of a 39-base pair duplex within cancer cells, selectively killing them (Shir, A., and A. Levitzski. 2002). The 39-bp duplex formed by the oncogenic fusion entity and the anti-sense RNA partially activated the protein kinase PKR, which is involved in inhibition of protein synthesis and cell death. In healthy cells, binding between the anti-sense RNA and the non-fused wild-type mRNA yielded only a 20-bp or 19-bp duplex, which resulted in minimal PKR activation. In this approach, the duplex formed in the process of oncogene detection served as the binding site for the activation of PKR. As a result, in this approach, the length of the activating RNA duplex is limited to twice the length of the longest duplex that does not activate PKR; this in turn limits the extent of PKR activation and the efficacy of a corresponding therapy.

A new approach to selective PKR activation has been developed based on the mechanism of HCR. Metastable RNA hairpins interact upon exposure to a target molecule to form long nicked polymers that subsequently activate PKR. The target molecule is preferably a mutant mRNA molecule associated with cancer. Activation of PKR leads to the inhibition of protein synthesis and to cell death (Jagus, R. et al. *The International Journal of Biochemistry* 31:123-138 (1999); Williams, B. R. G. *Oncogene* 18:6112-6120 (1999); which are incorporated herein by reference in their entirety). By transducing a detection binding event into the formation of a distinct activation domain, HCR hairpins can be used that bind minimal nucleic acid sequences but generate longer activation duplexes with multiple PKR binding domains (FIG. 5), leading to greater specificity and increased PKR activity. As a result, PKR is more effectively activated in target cells since the length of the activation duplexes is not limited as it is in the prior art approach described above. HCR is thus envisioned as a superior approach for activation of PKR for the purpose of triggering the death of diseased cells.

SUMMARY OF THE INVENTION

The invention relates generally to methods, compositions and kits to initiate hybridization chain reaction using RNA hairpin monomers to create RNA polymers that are able to activate the protein kinase PKR. The methods, compositions and kits can be used with samples and cell populations containing a target of interest. For example, RNA polymers can be created using RNA hairpin monomers that polymerize in the presence of a mRNA molecule associated with a disease or disorder, such as cancer.

In some embodiments, methods of activating the RNA-dependent protein kinase PKR are provided. A sample comprising PKR is contacted with a first RNA hairpin monomer comprising an initiator complement region and a second RNA hairpin monomer comprising a propagation region that is substantially complementary to a portion of the first monomer. The monomers are preferably metastable, such that a double-stranded RNA polymer comprising the first and second monomers is only formed upon binding of an initiator to the initiator complement region of the first monomer. The dsRNA polymer is preferably greater than 35 bp in length and thus is able to activate PKR in the sample.

The initiator is preferably able to bind to the initiator complement region of the first monomer and stimulate polymerization when a target is present in the sample. The target is preferably associated with a disease or disorder, and may be, for example, a nucleic acid such as an mRNA. In some embodiments the initiator is a portion of a target nucleic acid. In other embodiments the initiator is part of an initiation trigger such as a nucleic acid probe. Upon binding of a nucleic acid probe to a target nucleic acid sequence the initiator is made available to bind to the first monomer and stimulate polymerization of the monomers. In other embodiments the initiator comprises a recognition molecule such that upon binding of the recognition molecule to the target the initiator is made available to bind to the first monomer and stimulate polymerization. The recognition molecule may be, for example, an aptamer. In such embodiments, appropriate targets can include, but are not limited to, proteins, carbohydrates, lipids and small molecules, as well as nucleic acids.

In some embodiments, where the target is a nucleic acid sequence, the method of activating PKR can further include contacting the sample with at least one accessory molecule including a DNA molecule that binds to regions flanking the initiator portion of a target nucleic acid sequence.

In another aspect of the invention, methods are provided for treating a disease or disorder. Stimulation of PKR leads to reduction of translation and cell death. Thus, diseased cells can be targeted by stimulating PKR specifically in cells containing targets associated with a disease or disorder. In some embodiments, a disease or disorder is treated by providing a first RNA hairpin monomer to a cell comprising a target nucleic acid associated with the disease or disorder. A second RNA hairpin monomer is provided to the cell, wherein the second monomer comprises a propagation region that is substantially complementary to a portion of the first monomer. The first and second monomers polymerize in the presence of the target nucleic acid to form an RNA polymer that in turn activates PKR, leading to reduced translation, reduced cell growth, and cell death. The methods can be carried out in vivo or in vitro. The monomers may be provided to a cell, for example, in liposomes. The target nucleic acid sequence may be, for example, an mRNA associated with a cancer or a nucleic acid associated with HIV.

In yet another aspect of the invention, kits are provided for activating PKR in a sample comprising a target nucleic acid and PKR. The target nucleic acid may be, for example, associated with a disease or disorder such as cancer or HIV infection. The kits preferably comprise a first RNA hairpin monomer comprising an initiator complement region and a second RNA hairpin monomer comprising a propagation region that is complementary to a portion of the first monomer. In some embodiments the initiator complement region is complementary to an initiator portion of the target nucleic acid. The RNA hairpin monomers preferably have a stem that is from about 10 to 35 base pairs in length and a loop of at least about 3 base pairs. The kits may comprise additional components, such as an accessory DNA molecule that is complementary to a portion of the target nucleic acid molecule that flanks the initiator portion. The kits may also comprise a carrier that facilitates introduction of the monomers into a cell. In some embodiments an initiation trigger is also provided, wherein an initiator portion of the trigger is complementary to the initiator complement region of the first monomer and is made available upon biding of the trigger to the target. The initiation trigger may also comprise a recognition molecule, such as an aptamer.

BRIEF DESCRIPTION OF THE DRAWINGS

FIG. 1A shows two hairpins, labeled H1 and H2, that are metastable in the absence of initiator I. The hairpins comprise sticky ends 'a' and 'c*', respectively. Potential energy is stored in the hairpin loops.

FIG. 1B shows how a single initiator strand 'I' can nucleate or bind to the sticky end of H1 and displace one arm to open the hairpin. This frees up the bases that were trapped in the hairpin, allowing them to perform a similar displacement reaction on H2.

As illustrated in FIG. 1C, the newly exposed c region of H1 nucleates at the sticky end of H2 and opens the hairpin to expose a region on H2 (a*) that is identical in sequence to the initiator I. As a result, each copy of I can propagate a chain reaction of hybridization events between alternating H1 and H2 hairpins to form a nicked double helix, thereby amplifying the signal of initiator binding. The process can continue until the monomers (H1 and H2) are exhausted. At each step, energy is gained from the hybridization of 'a' or 'c'.

FIG. 4 shows how HCR-RNA monomers can be designed to polymerize by HCR upon exposure to a target.

FIG. 7 shows the results of PKR activation studies by RNA-HCR for (a) Ewing's sarcoma and (b) glioma.

DETAILED DESCRIPTION OF THE PREFERRED EMBODIMENT

Hybridization Chain Reaction (HCR) is a method for the triggered hybridization of nucleic acid molecules starting from metastable monomer hairpins or other metastable nucleic acid structures. See, for example, Dirks, R. and N. Pierce, Proc. Natl. Acad. Sci. USA 101(43): 15275-15278 (2004), and U.S. patent application Ser. No. 11/087,937, filed Mar. 22, 2005 (published as U.S. Publication No. 2005-0260635 on Nov. 24, 2005), each of which is incorporated herein by reference in its entirety. HCR does not require any enzymes and can operate isothermally.

In one embodiment of HCR, two or more metastable monomer hairpins are used. The hairpins preferably comprise loops that are protected by long stems. The loops are thus resistant to invasion by complementary single-stranded nucleic acids. This stability allows for the storage of potential energy in the loops. Potential energy is released when a triggered conformational change allows the single-stranded bases in the loops to hybridize with a complementary strand, preferably in a second hairpin monomer.

Figure 1:
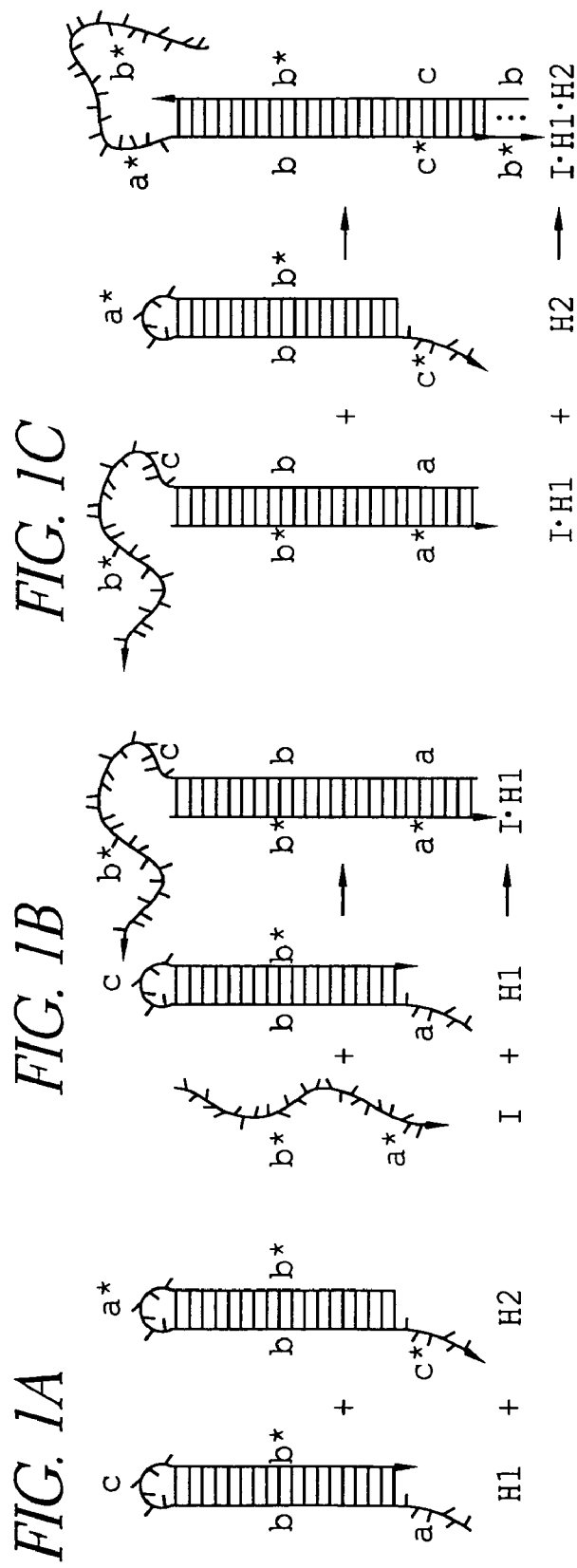
FIG. 1A-C schematically illustrates one embodiment of an HCR system. Each letter represents a segment of nucleic acids. Letters marked with a * are complementary to the corresponding unmarked letter.

Each monomer is caught in a kinetic trap, preventing the system from rapidly equilibrating. That is, pairs of monomers are unable to hybridize with each other in the absence of an initiator. Introduction of an initiator causes the monomers to undergo a chain reaction of hybridization events to form a nicked helix (see FIGS. 1A-C).

Methods and compositions using RNA-based HCR for forming double-stranded (ds) RNA polymers and for stimulation of PKR activity by the dsRNA polymers are provided. HCR is well-suited for this type of application since it can be used for the specific detection and/or treatment of targets associated with a disease or disorder. The target, which is found preferably exclusively in diseased cells or to a greater extent in diseased cells than in healthy cells, acts as a trigger for HCR of two or more RNA monomers. The polymers containing dsRNA can be detected, for example, by any of the methods described in U.S. patent application Ser. No. 11/371,347 or in U.S. patent application Ser. No. 11/371,346, each of the foregoing which is herein incorporated by reference in its entirety. Such detection could be used in diagnosis, for example, to confirm the presence of the disease or disorder in a patient. Polymer formation in the presence of a target associated with a disease or disorder can also be used therapeutically. In some embodiments, the formation of HCR dsRNA polymers in targeted cells activates PKR, leading to inhibition of translation, reduction of cell growth and cell death. In this way, a disease or disorder can be treated and/or prevented by targeting diseased cells.

Diseases contemplated for treatment in embodiments of the invention include any disease in which a target molecule associated with the disease is present in a cell and can initiate polymerization of HCR hairpin monomers, and wherein inhibition of translation and/or cell death would be beneficial to a patient. The target can itself stimulate HCR polymerization or act on an initiation trigger to initiate HCR. Preferred embodiments include, but are not limited to, diseases in which the target is a nucleic acid molecule. In some embodiments, the nucleic acid molecule is an mRNA molecule associated with a disease or disorder, such as a mutant mRNA molecule. However, disease-associated HCR targets can be, for example and without limitation, nucleic acid sequences, proteins, peptides, lipids, carbohydrates and small molecules.

In some embodiments, the disease to be treated is a type of cancer, such as, for example, leukemia, carcinoma, lymphoma, astrocytoma, sarcoma and particularly Ewing's sarcoma, glioma, retinoblastoma, melanoma, Wilm's tumor, bladder cancer, breast cancer, colon cancer, hepatocellular cancer, pancreatic cancer, prostate cancer, lung cancer, liver cancer, stomach cancer, cervical cancer, testicular cancer, renal cell cancer, and brain cancer.

In other embodiments, the disease to be treated is associated with infection by an intracellular parasite. For example, the intracellular parasite may be a virus such as, for example, an adenovirus, cytomegalovirus, Epstein-Barr virus, herpes simplex virus, human herpesvirus 6, varicella-zoster virus, hepatitis viruses, papilloma virus, parvovirus, polyomavirus, measles virus, rubella virus, human immunodeficiency virus (HIV), or human T cell leukemia virus. In other embodiments, the intracellular parasite may be a bacterium, protozoan, fungus, or a prion. More particularly, the intracellular parasite can be, for example, *Chlamydia, Listeria, Salmonella, Legionella, Brucella, Coxiella, Rickettsia, Mycobacterium, Leishmania, Trypanasoma, Toxoplasma*, and *Plasmodium*.

In some embodiments, HCR-RNA monomers polymerize in the presence of target molecules such as cancer related mRNA sequences or viral nucleic acids and form polymers that activate PKR. Activation of PKR leads to general inhibition of translation and cell death in cells comprising the disease-associated target (diseased cells).

In some embodiments, the target molecule is a sequence that is necessary for the life cycle or replication of a virus, such as, for example, gene expression of the virus and the expression of a cellular receptor or co-receptor necessary for viral replication. In some particular embodiment of the invention, the virus is the human immunodeficiency virus (HIV). The target sequence may be, for example, selected from the group consisting of Rev, Gag, Pol, LTRs, TAR, RRE, Ψ, att, pbs, ppt and other essential DNA and RNA cis-regulatory elements. In one embodiment of the invention, the target molecule is an expressed region of the HIV viral genome, for example, a portion of the 9-kb transcript of the integrated HIV virus, or any of the variously spliced mRNA transcripts of HIV (Schwartz, S; Felber, B K; Benko, D M; Fenya, E M; Pavlakis, G N. Cloning and functional analysis of multiply spliced mRNA species of human immunodeficiency virus type 1. *J. Virol.* 1990; 64(6): 2519-29). Target regions within the HIV transcripts can be chosen to correspond to any of the viral genes, including, for example, HIV-1 LTR, vif; nef and rev.

The invention also includes methods of treating a patient suffering from a disease or disorder such as a cancer or a viral infection. In some embodiments the methods comprise administering to target cells in the patient, such as tumor cells, an effective amount of HCR monomers, one of the monomers having an initiator complement region having at least 90% homology and preferably identical to a target region of a nucleic that is associated with the disease, such as an mRNA associated with the cancer or a viral-associated nucleic acid. For example, the HCR RNA monomers may be designed to polymerize in the presence of an oncogenic mRNA or a viral gene transcript.

In one embodiment, the patient to be treated is infected with the human immunodeficiency virus. A target cell is removed from a patient. In a preferred embodiment, the target cell is a CD34-positive hematopoietic stem cell. Such stem cells can be purified by one of skill in the art. Methods for such purification are known and taught for example in U.S. Pat. Nos. 4,965,204; 4,714,680; 5,061,620; 5,643,741; 5,677,136; 5,716,827; 5,750,397 and 5,759,793. HCR RNA monomers that are able to polymerize in the presence of a target in the viral genome are transfected into the isolated CD34-positive stem cells. The treated stem cells are then reintroduced into the patient.

DEFINITIONS

"Nucleic Acids" as used herein means oligomers of DNA or RNA. Nucleic acids may also include analogs of DNA or RNA having modifications to either the bases or the backbone. For example, nucleic acid, as used herein, includes the use of peptide nucleic acids (PNA). The term "nucleic acids" also includes chimeric molecules.

The term "sticky end" refers to a nucleic acid sequence that is available to hybridize with a complementary nucleic acid sequence. The secondary structure of the "sticky end" is such that the sticky end is available to hybridize with a complementary nucleic acid under the appropriate reaction conditions without undergoing a conformational change. Typically the sticky end is a single stranded nucleic acid.

"Monomers" are individual nucleic acid oligomers. Typically, at least two monomers are used in hybridization chain reactions, although three, four, five, six or more monomers may be used. In some embodiments more than two monomers are utilized, such as in HCR systems displaying quadratic and exponential growth. Typically each monomer comprises at least one region that is complementary to at least one other monomer being used for the HCR reaction. The makeup of the monomers is described in more detail below.

A first monomer in a monomer pair typically comprises an initiator complement region that is complementary to a portion of an initiator molecule. The initiator complement region is preferably a sticky end. Other embodiments of the first monomer comprise a recognition molecule that binds or interacts with an initiator molecule. Interaction of the initiator to the initiator complement region or to the recognition molecule begins an HCR reaction.

In addition, the second monomer in the pair preferably comprises a propagation region that is able to hybridize to a complementary region of another monomer, preferably another copy of the first monomer, to continue the HCR reaction begun by the initiator. The propagation region can be, for example, the loop region of a hairpin monomer as described below. In one embodiment the propagation region on the second monomer is identical to the portion of a nucleic acid initiator molecule that is complementary to the initiator complement region of the first monomer.

The propagation region on the second monomer is preferably only available to interact with the initiator complement region of the first monomer when an HCR reaction has been started by an interaction between the initiator and the first monomer. That is, the propagation region becomes available to hybridize to a complementary region of another monomer, preferably another copy of the first monomer, when one copy of the first monomer has already hybridized to a second monomer, as discussed in more detail below.

Preferred monomers are "metastable." That is, in the absence of an initiator they are kinetically disfavored from associating with other monomers comprising complementary regions. "HCR" monomers are monomers that are able to assemble upon exposure to an initiator to form a polymer.

As used herein, "polymerization" refers to the association of two or more monomers to form a polymer. The "polymer" may comprise covalent bonds, non-covalent bonds or both. For example, in some embodiments two species of monomers are able to hybridize in an alternating pattern to form a polymer comprising a nicked double helix. The polymers are also referred to herein as "HCR products."

An "initiator" is a molecule that is able to initiate the polymerization of monomers. Initiators include molecules that comprise a region that hybridizes, binds or otherwise interacts with the initiator complement region or recognition molecule of an HCR monomer. In some embodiments, the initiator is a combination of molecules that can initiate HCR polymerization. In other embodiments, the initiator is a portion of an initiation trigger, where interaction between the trigger and a target exposes the initiator to stimulate HCR polymerization. Preferred initiators comprise a nucleic acid region that is complementary to the initiator complement region of an HCR monomer.

A "target" is a molecule of interest, or a combination of molecules of interest, whose presence can trigger HCR polymerization. Preferred targets are associated with a disease or disorder. In some embodiments, the target comprises an initiator that is able to stimulate HCR polymerization of the monomers. In other embodiments, the target is a molecule, or combination of molecules, that is recognized by the initiator, or an initiation trigger comprising the initiator, such that the initiator is made available to induce HCR polymerization.

A "target cell" is a cell that contains a target associated with a disease or disorder. The target is typically one that is not normally found in healthy cells or that is found to a greater extent in diseased cells than in healthy cells. The target can act as the initiator for HCR when HCR monomers are introduced into the target cell. Examples of target cells include cells that contain a nucleic acid signature for a disease, such as, for example, mutant mRNA or fusion mRNA entities. Other examples include, but are not limited to, cells that contain higher-than-background levels of peptides, polypeptides, antibodies or fragments thereof, signal cascade molecules, viral particles, bacteria and parasitic organisms.

Monomers

Two or more distinct species of nucleic acid monomers are preferably utilized in an HCR reaction. In the methods described herein, the monomers are preferably RNA monomers. Each monomer species typically comprises at least one region that is complementary to a portion of another monomer species. However, the monomers are designed such that they are kinetically trapped and the system is unable to equilibrate in the absence of an initiator molecule that can disrupt the secondary structure of one of the monomers. Thus, the monomers are unable to polymerize in the absence of the initiator. Binding of an initiator species to a monomer triggers a chain reaction of alternating kinetic escapes by the two or more monomer species resulting in formation of a polymer. In the examples below, two RNA hairpin monomers polymerize in the presence of an initiator to form a nicked, double-stranded RNA helix.

In a preferred embodiment, two or more monomer species are employed that have a hairpin structure. The hairpin monomers preferably comprise loops protected by long stems. In other embodiments, monomers with a different secondary structure are provided. However, the secondary structure is preferably such that the monomers are metastable under the reaction conditions in the absence of an initiator. In the presence of an initiator, the secondary structure of a first monomer changes such that it is able to hybridize to a sticky end of a second monomer species. This in turn leads to a change in the secondary structure of the second monomer, which is then able to hybridize to another monomer and continue the process. In preferred embodiments, the second monomer is able to hybridize to another copy of the first monomer to continue the polymerization process. In this way, once a single copy of the first monomer interacts with a single copy of the initiator, a chain reaction is produced such that the monomers are able to assemble into a polymer comprising alternating monomer species. Thus, the presence of multiple target molecules, multiple polymers are produced.

A number of criteria can be used to design the monomers to achieve the desired properties. These include, for example and without limitation, sequence symmetry minimization, the probability of adopting the target secondary structure at equilibrium, the average number of incorrect nucleotides at equilibrium relative to the target structure, and hybridization kinetics.

Monomers can be synthesized using standard methods, including commercially available nucleic acid synthesizers or obtained from commercial sources such as Integrated DNA Technologies (Coralville, Iowa).

In preferred embodiments, the monomers are RNA monomers. In some embodiments, the monomers contain a fluorophore, luminescent molecule, calorimetric compound or other component that allows the resulting polymers to be visualized.

In preferred embodiments, at least two RNA hairpin monomers are utilized as illustrated in FIG. 1A. The monomers each preferably comprise a sticky end (a and c*, respectively), a first complementary segment (b and b*, respectively), a loop segment (c and a*, respectively), and a second complementary segment (b and b*, respectively). The first and second complementary segments are also referred to as "stems" and together form a duplex region.

The first monomer (H1) preferably comprises a sticky end a that is complementary to a first nucleic acid portion a* of an initiator (I; FIG. 1B). This sticky end is referred to herein as the "initiator complement region." The initiator may be, for example, a target of interest, a nucleic acid that is able to contact the first monomer only in the presence of a target of interest, or any cellular component (such as, for example, a nucleic acid sequence) that is found only in target diseased cells or to a lesser extent in healthy cells, as discussed in more detail below.

The second monomer (H2) preferably comprises a sticky end c* that is complementary to a portion of the first monomer that becomes accessible upon initiator binding. Preferably the sticky end c* is complementary to the loop segment c of the first monomer (FIG. 1A). The loop segment c of the first monomer is preferably not available to hybridize with sticky end c* of the second monomer in the absence of initiator.

The first and second complementary segments (b and b*) in the first and second monomers are typically substantially identical. That is, the first complementary segment b of the first monomer (H1) is able to hybridize to the second complementary segment b* of the second monomer (H2).

The first complementary segment of each monomer is also able to hybridize to the second complementary segment of the same monomer to form the hairpin structure. For example, as shown in FIG. 1A, the first monomer (H1) comprises a first complementary segment b that is able to hybridize to the second complementary segment b*. In the absence of an initiator, the first and second complementary segments of each monomer are generally hybridized to form a duplex region of the metastable monomer.

In some embodiments, the first complementary segment b of the first monomer is also complementary to a portion b* of the initiator, such that upon hybridization of the initiator region a* to the sticky end a (the initiator complement region) of the first monomer H1, one arm of the hairpin structure is displaced. This opens the hairpin and allows binding of the first complementary segent b to the second portion b* of the initiator strand (FIG. 1B). In other embodiments, a recognition molecule included within the first monomer can hybridize, bind or interact with at least a portion of the initiator such that one stem of the hairpin structure is displaced, allowing opening of the hairpin.

Recognition molecules include, without limitation, polypeptides, such as antibodies and antibody fragments, nucleic acids, aptamers, and small molecules. The use of a first HCR monomer bound to a recognition molecule is described in more detail below.

The loop segment c of the first monomer is also exposed by the opening of the hairpin and is able to bind to the sticky end c* of the second monomer H2, as illustrated in FIG. 1C. This opens the second monomer hairpin H2 and the second complementary segment b* of the first monomer is able to hybridize to the first complementary segment b of the second monomer H2.

This leaves the loop region a* and first complementary region b* of the second monomer H2 exposed (FIG. 1C). The sticky end a of another first monomer (H1) species is able to bind to the exposed loop region a* of the second monomer H2, thus opening the H1 hairpin and continuing the process described above. Because the loop region a of the second monomer acts as an initiator on a second H1 monomer and allows the process to continue in the absence of further initiator, it is referred to as the propagation region.

At each step, energy is gained from the hybridization of the sticky end of the monomer. The result is a nicked, double helix RNA polymer comprising alternating H1 and H2 fragments. This process preferably continues in a chain reaction until all of one or both of the monomer species is used up, or the reaction is stopped by some other mechanism. If desired, the nicks in the nucleic acid polymer structures that result from HCR can by ligated (for example, using ligase).

Because of the self-propagating nature of the reaction, each copy of the initiator species can begin the chain reaction. Further, as long as there is a fixed supply of monomers the average length of the resulting polymers is inversely related to the initiator concentration. The concentration of the monomers can be adjusted to ensure that the polymers are of sufficient length to activate one or more PKR molecules, more preferably two or more PKR molecules, for each target that is detected.

The length of the loop, stem and sticky ends of the monomers can be adjusted, for example to ensure kinetic stability in particular reaction conditions and to adjust the rate of polymerization in the presence of initiator. In one preferred embodiment the length of the sticky ends is the same as the length of the loops. In other embodiments the sticky ends are longer or shorter than the loops. However, if the loops are longer than the sticky ends, the loops preferably comprise a region that is complementary to the sticky end of a monomer.

In some preferred embodiments the length of the loops is short relative to the stems. For example, the stems may be two or three times as long as the loops.

The loop regions are preferably between about 1 and about 100 nucleotides, more preferably between about 3 and about 30 nucleotides and even more preferably between about 4 and about 7 nucleotides. In one embodiment the loops and sticky ends of a pair of hairpin monomers are about 6 nucleotides in length and the stems are about 18 nucleotides long.

Other refinements to the system stabilize the monomer hairpins to help prevent HCR in the absence of an initiator. This can be achieved, for example, via super-stable hairpin loop sequences (Nakano et al. *Biochemistry* 41:14281-14292 (2002), herein incorporated by reference in its entirety), with ostensible structural features that could further inhibit direct hybridization to the hairpin. In other embodiments hairpin loops are made to be self-complementary at their ends. This self-complementation "pinches" the hairpin loops, making them shorter. However, if the reactive sticky ends of each monomer are complementary to the loop regions on the opposite monomer, as described above, they will have a slight propensity to close up, thereby slowing down the reaction. This feature can be utilized if a slower reaction is desired. Completely self-complementary hairpins can also be used, for example if the monomer hairpins are forming dimers with interior loops that are more easily invaded than their hairpin counterparts.

Reaction conditions are preferably selected such that hybridization is able to occur, both between the initiator and the sticky end of a first monomer, and between the complementary regions of the monomers themselves. The reaction temperature does not need to be changed to facilitate the hybridization chain reaction. That is, the HCR reactions are isothermic. They also do not require the presence of any enzymes.

Variations

There are many possible variations to HCR that may improve its speed, stability and ability to activate PKR. The system illustrated in FIG. 1 and discussed above exhibits linear growth in response to initiator. However, increasing the rate of polymer growth can enhance the ability to respond to the presence of low copy number targets, such as a single target molecule in a large volume. For example, monomers can be designed to undergo triggered self-assembly into branched structures exhibiting quadratic growth or dendritic structures exhibiting exponential growth. The exponential growth is limited by the available space such that it decreases to cubic amplification as the volume around the initiator fills. However, if chain reactions products are able to dissociate, exponential growth can be maintained until the supply of monomers is exhausted.

In order to achieve non-linear growth, 3 or more HCR monomers can be used. In preferred embodiments, at least 4 HCR monomers are used. In some embodiments, at least one monomer in a primary monomer pair incorporate a nucleic acid trigger segment that is complementary to the exposed sticky end of one of the monomers from a secondary set of HCR monomers. Upon exposure to the nucleic acid that is to be detected, the set of primary monomers undergoes HCR to form a polymer with a periodic single stranded trigger region. Thus the trigger nucleic acid is exposed, leading to a polymerization chain reaction in the secondary set of monomers. In other embodiments, both the primary and secondary set of monomers includes a trigger segment, such that exponential growth is achieved. Exemplary schemes are presented and described in U.S. patent application Ser. No. 11/087,937 (published as U.S. Publication No. 2005-0260635), herein incorporated by reference in its entirety.

Initiator

The initiator is preferably a nucleic acid or other molecule that is able to contact the first monomer and trigger polymerization only in the presence of a target associated with a disease or disorder. The target can be, but is not limited to, any of the following: a nucleic acid sequence, a peptide, a polypeptide, an antibody or fragment thereof, a signal cascade molecule, a lipid, a carbohydrate, a fused entity, a viral particle, a bacterium or a parasitic organism. In preferred embodiments, the initiator is at least a portion of the target. For example, in one embodiment, the initiator can be a portion of a nucleic acid associated with a disease or disorder.

The initiator is preferably a nucleic acid molecule. The nucleic acid initiator comprises an initiator region that is complementary to a portion of an HCR monomer, preferably a portion of the monomer that is available for hybridization with the initiator while the monomer is in its kinetically stable state. The initiator also preferably comprises a sequence that is complementary to a portion of the monomer adjacent to the sticky end such that hybridization of the initiator to the sticky end causes a conformational change in the monomer and begins the HCR chain reaction. For example, the initiator may comprise a region that is complementary to the first complementary region of the HCR monomer, as described above and illustrated in FIG. 1.

In the preferred embodiments, the sequence of the initiator is complementary to the sticky end (initiator complementary region) and first complementary region of a first monomer. As described above, in some embodiments this will also influence the sequence of the second complementary region and the loop of the second monomer species.

Figure 4A:
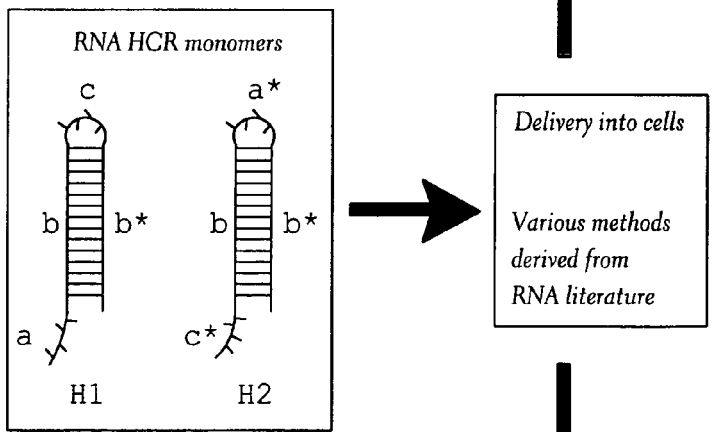
FIG. 4(a) illustrates HCR-RNA hairpin monomers.
Figure 4B:
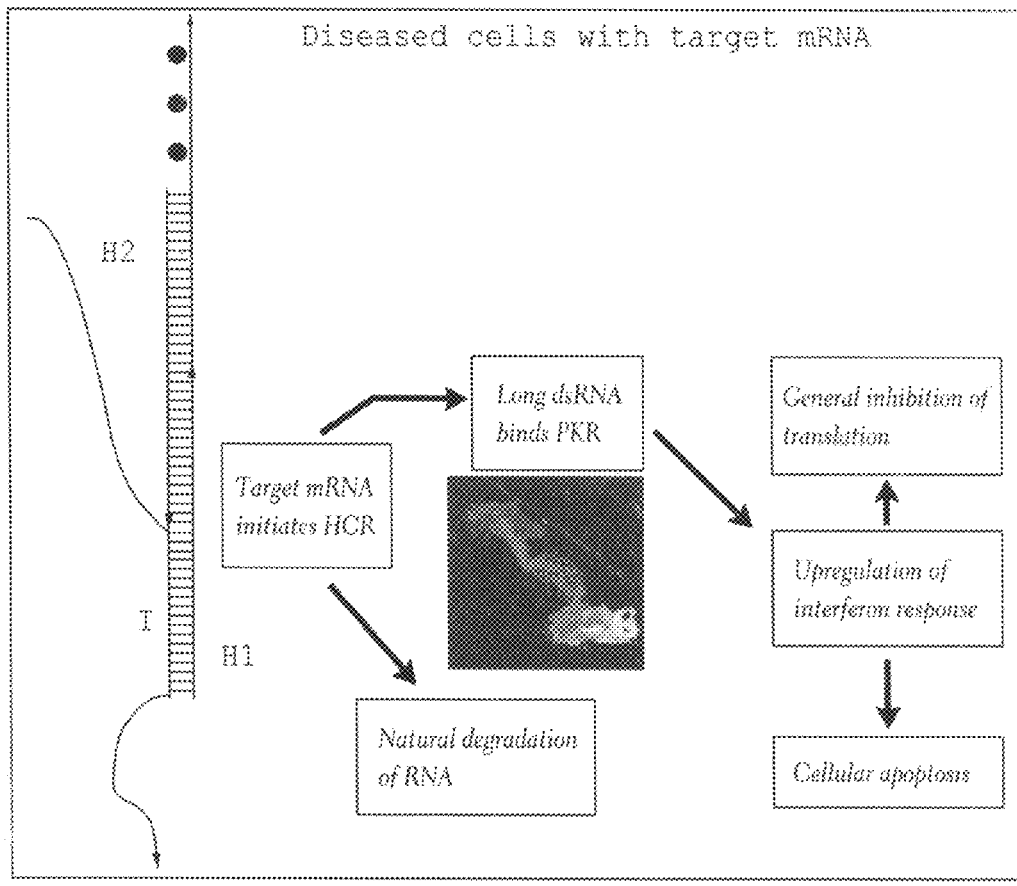
FIG. 4(b) demonstrates delivery of the RNA hairpin monomers ('H1' and 'H2') to cells containing a target mRNA sequence ('I') and the long double-stranded RNA (dsRNA) polymers that are consequently formed. These polymers can bind to and activate PKR, a human RNA-activated protein kinase. Once bound to dsRNA, dimerized PKR molecules activate each other via phosphorylation and then set in motion a response that inhibits translation and leads to cell death.
Figure 4C:
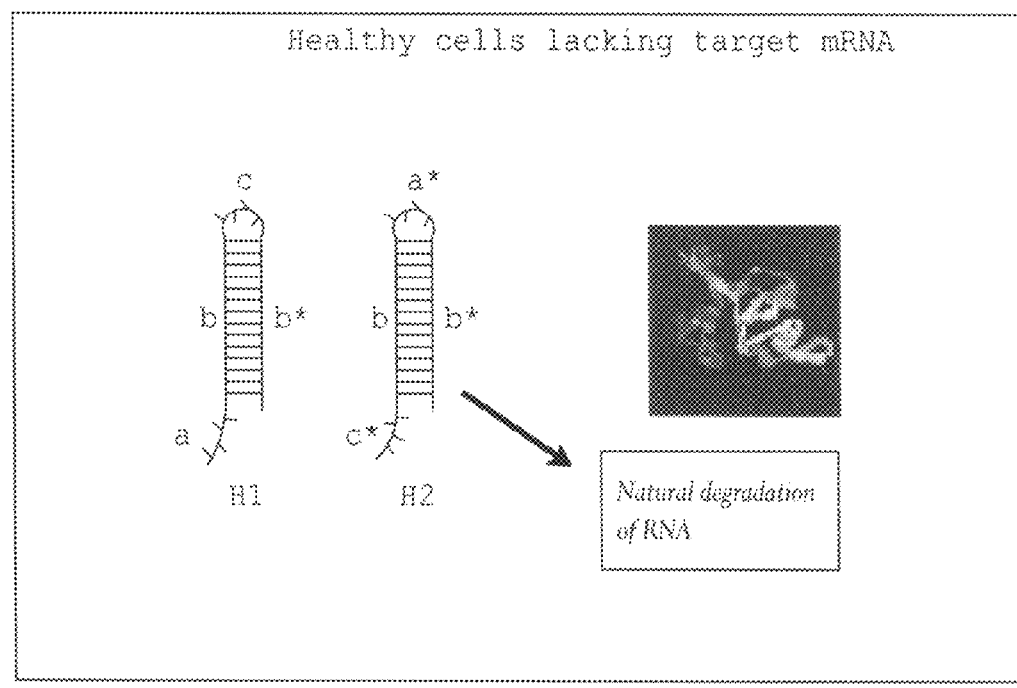
FIG. 4(c) shows that in cells lacking a target sequence, the HCR hairpins will not activate PKR and hence will not shut down protein synthesis or cause cell death.
Figure 5:
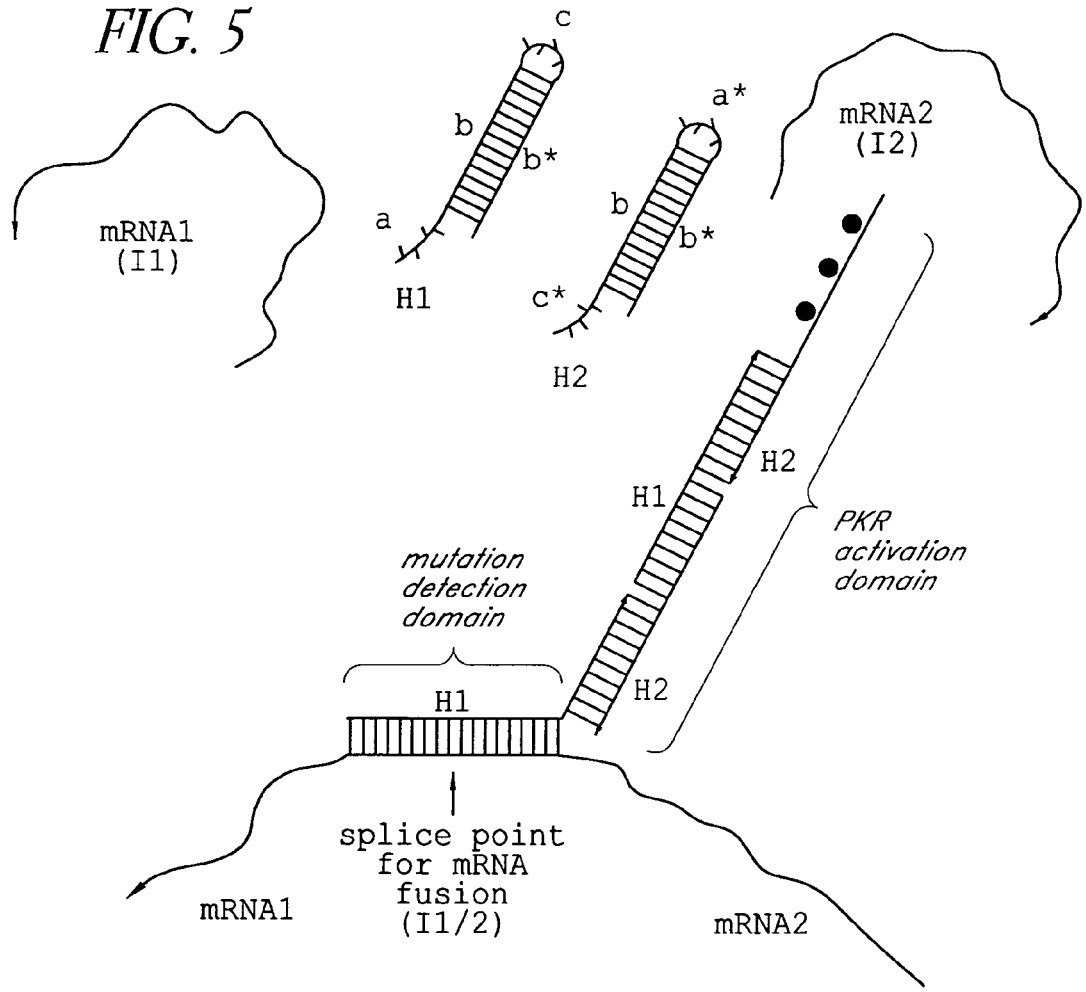
FIG. 5 shows how HCR using RNA can provide a sensitive approach for activation of PKR. An RNA hairpin monomer ('H1') is designed that detects the fusion entity ('I1/2') within a diseased cell. Binding between H1 and I1/2 displaces one arm of H1 to open the hairpin. The bases trapped in the hairpin are now free to bind to a complementary region in a second RNA hairpin monomer ('H2') and perform a similar displacement reaction as described in FIG. 1. The formation of the HCR product by polymerization between H1 and H2 is effective at activating PKR. Given a sufficient ratio of monomers to target molecules, polymers that provide binding sites for multiple PKR molecules can be formed.

In some embodiments the initiator is a target nucleic acid or a portion of a target nucleic acid that is to be detected in a sample (FIG. 4). In this case, the sequence of the target nucleic acid is taken into consideration in designing the HCR monomers. For example, the initiator complement region, preferably a sticky end, of one monomer ('H1') is designed to be complementary to a portion of the target nucleic acid sequence ('I'). The initiator complement region is preferably at least 80%, more preferably at least 90%, 95% or higher, identical to the initiator sequence. In preferred embodiments, the initiator sequence is at least 2, 3, 4, 5, or 10 or more bases in length.

Similarly, a region adjacent to the sticky end of the same monomer can be designed to be complementary to a second region of the target sequence as well. Because the second monomer ('H2') will hybridize to the first monomer ('H1'), the sequence of the second monomer will also reflect at least a portion of the sequence of the target nucleic acid and/or the initiator. In preferred embodiments, the initiator is an mRNA target sequence or a portion of an mRNA target sequence, for example, a portion of a mutant mRNA sequence that comprises a mutation associated with a disease or disorder. Embodiments also include specific combinations of mRNA sequences.

Figure 2:
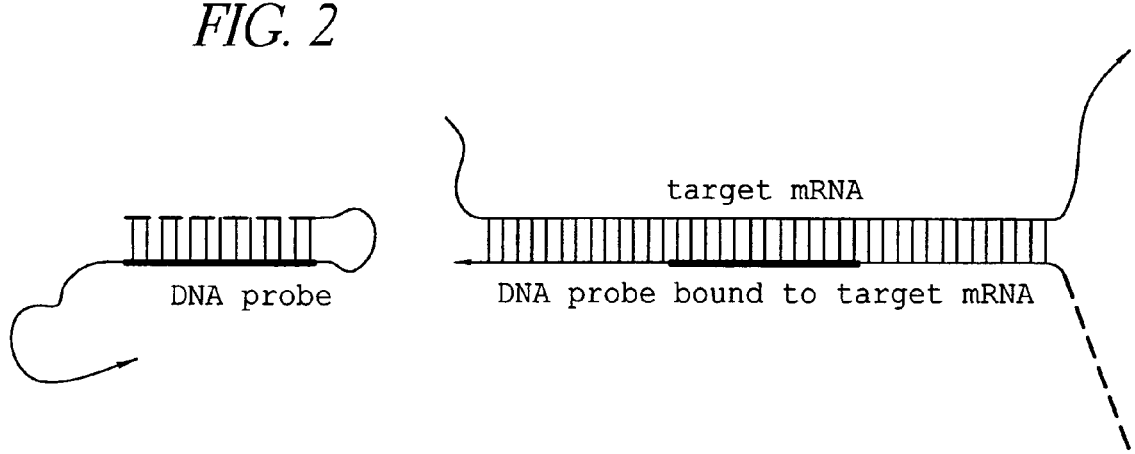
FIG. 2 shows a DNA probe molecule that contains an initiator sequence (heavy dashed line) that initiates RNA-HCR upon binding of the probe to an mRNA target. The single stranded regions on either side of the duplex region of the probe compete with native base pairing in the target mRNA to facilitate triggering of RNA-HCR.

In other embodiments, the initiator comprises at least a portion of a nucleic acid that is part of an "initiation trigger" such that the initiator is made available when a predetermined physical event occurs. In the preferred embodiments, that predetermined event is the presence of a target associated with a disease or disorder. In each of these embodiments, the initiator is preferably associated with a molecule that is responsive to the presence of the target. Thus, the initiator and the associated molecule together form the initiation trigger. For example, the initiator may be associated with a molecule that undergoes a conformational change in response to binding to the target (FIG. 2). The conformational change exposes the initiator and thereby stimulates polymerization of the HCR monomers. In other embodiments, however, the initiation trigger comprises a single nucleic acid. The initiator region of the nucleic acid is made available in the presence of the target.

The structure of the initiation trigger is preferably such that when the target is not present (or the other physical event has not occurred), the initiator is not available to hybridize with the sticky end of a monomer. The target frees the initiator such that it can interact with a metastable monomer, triggering the HCR polymerization reactions described above. In some embodiments, the target causes a conformational change in the trigger that allows the initiator to interact with the monomer.

Figure 3:
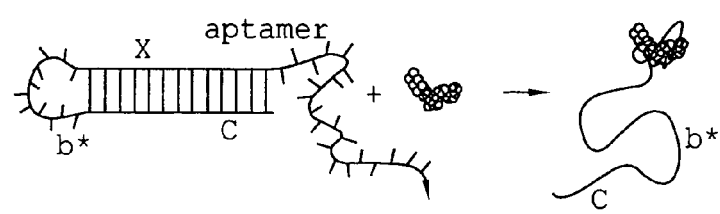
FIG. 3 illustrates an aptamer HCR initiation trigger mechanism for the detection of a target molecule, such as a peptide. Binding of the aptamer to the target molecule induces a conformational change that exposes a sticky end initiator that can initiate HCR.

The initiator may be part of a trigger comprising a nucleic acid initiator that is linked to or associated with a recognition molecule, such as an aptamer, that is capable of interacting with a target of interest (FIG. 3). The trigger is designed such that the initiator is unavailable to stimulate HCR in the absence of the target. When the target interacts with the recognition molecule, the initiator is able to stimulate HCR. Preferably, the recognition molecule is one that is capable of binding the target.

Recognition molecules include, without limitation, polypeptides, antibodies and antibody fragments, nucleic acids, aptamers, and small molecules. The use of an initiator bound to an aptamer is described in more detail below.

In some particular embodiments, amplification is achieved by coupling a first HCR monomer to a recognition molecule such as, for example, a nucleic acid aptamer trigger. An aptamer is identified that is able to specifically bind the target. In such embodiments, the target is not limited to a nucleic acid but may be, for example, a polypeptide or small molecule. The aptamer is linked to the HCR monomer in such a way that the initiator is unavailable to stimulate HCR in the absence of target binding to the aptamer.

Preferably, conformational changes in the first HCR monomer-aptamer secondary structure expose the first complementary segment. In one embodiment, such an aptamer trigger is a hairpin nucleic acid that comprises a first complementary segment that is able to hybridize to a second complementary segment of a second HCR monomer. The hairpin aptamer trigger may also comprise a region that enhances the stability of the hairpin in the absence of aptamer binding to the initiator, such as a nucleic acid region in one arm of the hairpin that is complementary to a region of the other arm.

FIG. 2 illustrates how a DNA probe molecule containing a trigger sequence (heavy dashed line) can initiate RNA-HCR polymerization upon binding to a target mRNA molecule. The single stranded regions on either side of the duplex region of the probe compete with native base pairing in the target molecule to facilitate triggering of the polymerization reaction.

FIG. 3 depicts a scheme for HCR amplification using an aptamer construct that exposes an initiator strand upon binding to a target. The sticky end can act as a trigger for the HCR mechanism of FIG. 1 by opening hairpin H2. The region X is introduced to help stabilize the trigger in the absence of analyte. The region b* includes both the hairpin loop and the portion of the stem complementary to X. This trigger mechanism is based on conformational changes in the aptamer secondary structure (Li, Y. *Journal of the American Chemical Society* 125:4771-4778 (2003), herein incorporated by reference in its entirety) that make the initiator strand available to stimulate HCR.

Stimulation of PKR Activity Using RNA-Based HCR Monomers

Long stretches of double stranded RNA are known to trigger an interferon response in mammalian cells via the RNA-dependent protein kinase PKR. This is a part of a natural anti-viral response meant to inhibit translation when an infection is detected. This response inhibits cell growth, and leads to programmed cell death (apoptosis). Sufficiently short RNAs such as, for example, HCR hairpins with stems of approximate length 14, do not effectively induce an interferon response. Consequently, if RNA-based HCR hairpins are delivered to a mixed population of cells where some contain a specific target molecule and others do not, then HCR polymerization and a subsequent interferon response will only occur in cells containing the trigger and thus where RNA polymers are formed. In this way, inhibition of cell growth and/or cell death can be induced specifically in diseased cells, such as tumor cells, using HCR, while avoiding the the response in other cells. This technique can be used as a therapeutic to inhibit or kill diseased or cancerous cells, leaving healthy cells intact as unpolymerized RNA hairpins eventually degrade harmlessly via natural mechanisms.

HCR is therefore considered an effective strategy for activating PKR within target cells by forming long RNA HCR assemblies within the cells. Once an HCR product forms within a target cell, the HCR product serves as an activation domain to upregulate PKR, leading to subsequent inhibition of translation and apoptosis. Design of appropriate HCR hairpin monomers that do not themselves activate PKR, but activate PKR upon binding a target can be derived from target sequences well known in the art and available from literature reviews and disclosed in, for example, various databases (e.g. NCBI).

HCR can be performed using RNA hairpin monomers to detect a target associated with a disease or a disorder. In some embodiments, the target is associated with a membrane. In other embodiments, the target is a non-tethered entity. The target can be, for example, a nucleic acid associated with cancer, such as an mRNA associated with a cancer. In embodiments where the target is also the initiator, a first RNA hairpin with an initiator complement region hybridizes or binds the target. In embodiments where the target and initiator are distinct entities, recognition of the target by the initiator or by the trigger comprising the initiator allows binding between a first RNA hairpin comprising an initiator complement region and the initiator. Binding between the initiator complement region of the first hairpin and the initiator opens the hairpin to expose a sequence that is substantially complementary to the propagation region of a second RNA hairpin monomer.

Hybridization between the exposed sequence of the first hairpin monomer and the propagation region of the second hairpin monomer opens the second hairpin. This event exposes a sequence in the second hairpin that is substantially complementary to the initiator complement region on another copy of the first hairpin. Hybridization consequently occurs between the exposed sequence of the second hairpin and the initiator complement of another copy of the first hairpin, and the chain reaction continues as described until the supply of hairpin monomers is exhausted. The HCR product that forms is a nicked double-stranded RNA polymer. The double-stranded RNA products that form in cells containing the target are of a length that is sufficient to activate one or more PKR molecules per polymer product. In preferred embodiments, the RNA products comprise at least 35 base pairs. Activation of PKR can lead to inhibition of translation, inhibition of cell growth and to cell death.

Double-stranded RNA polymers formed by HCR are at least approximately 35 bp in length. In some embodiments, the RNA polymers are at least approximately 30 bp in length. In other embodiments, the RNA polymers are at least approximately 25 bp in length. In further embodiments, the RNA polymers are at least approximately 20 bp in length. In still other embodiments, the RNA polymers are at least approximately 15 bp in length.

In some embodiments, HCR is used to treat a patient suffering from a disease or disorder. Because HCR polymerization is specifically limited to those cells containing the target associated with the disease or disorder, the HCR monomers can be delivered to a multitude of cells, including healthy cells. Thus, general delivery of the monomers to a population of cells comprising cells containing a disease-associated target and wild-type cells is possible. HCR polymerization takes place in diseased cells containing the target, leading to the death of those cells in therapeutic treatments. In a particular embodiment, HCR polymerization occurs in target cells comprising an mRNA molecule associated with cancer, leading to the death of cancerous cells.

Delivery of HCR Monomers to Target Cells

HCR monomers and any accessory molecules, such as, for example, initiation triggers, can be formulated with any of a variety of carriers well known in the art to facilitate introduction into a cell. Suitable carriers for delivery of nucleic acids to cells are well known in the art and include, for example, polymers, proteins, carbohydrates and lipids. For example, a cyclodextrin-containing polymer can be used for the delivery of the nucleic acid HCR monomers. Commercial transfection reagents known in the art, such as, for example, LNCaP (Altogen Biosystems) or lipofectamine RNAiMax (Invitrogen), can be used.

Delivery of nucleic acids can be accomplished, for example, as described by Heidel (Heidel, J. D. 2005. Targeted, systematic non-viral delivery of small interfering RNA in vivo. Doctoral thesis, California Institute of Technology. 128 p., herein incorporated by reference in its entirety). Also contemplated within the scope of the subject matter are gene delivery systems as described by Felgner et al. (Felgner et al. 1997. *Hum Gene Ther* 8:511-512, herein incorporated by reference in its entirety), including cationic lipid-based delivery systems (lipoplex), polycation-based delivery systems (polyplex) and a combination thereof (lipopolyplex). Cationic lipids are described, for example, in U.S. Pat. Nos. 4,897,355 and 5,459,127, each of the foregoing which is herein incorporated by reference in its entirety. Proteins can also be used for HCR delivery, such as synthetic neoglycoproteins (Ferkol et al. 1993. *FASEB J* 7:1081-1091; Perales et al. 1994. *Proc Nat Acad Sci* 91:4086-4090; each of which is incorporated herein by reference in its entirety). epidermal growth factor (EGF) (Myers, EPO 0273085, incorporated herein by reference in its entirety), and other ligands for receptor-mediated gene transfer (Wu and Wu. 1987. *J Biol Chem* 262(10):4429-4432; Wagner et al. 1990. *Proc Natl Acad Sci USA* 87(9):3410-3414; Ferkol et al. 1993. *J. Clin Invest* 92(5):2394-2300; Perales et al. 1994. *Proc Natl Acad Sci USA* 91(9):4086-4090; Myers, EPO 0273085; each of which is incorporated herein by reference in its entirety).

Viral and viral vector-like delivery systems generally known in the art, such as those described, for example, in U.S. Pat. No. 7,0333,834; U.S. Pat. No. 6,899,871; U.S. Pat. No. 6,555,367; U.S. Pat. No. 6,485,965; U.S. Pat. No. 5,928,913; U.S. patent application Ser. No. 10/801,648; U.S. patent application Ser. No. 10/319,074, and U.S. patent application Ser. No. 09/839,698, each of which is herein incorporated by reference, are also contemplated for use in the present subject matter. In addition, standard electroporation techniques can be readily adopted to deliver HCR monomers.

Delivery of HCR monomers can occur in vivo or ex vivo. In some embodiments, cells can be removed from a patient, transfected with the monomers and returned to the patient for therapeutic effects. In other embodiments, HCR monomers can be delivered to cells in vivo such as by, for example, injection of the monomers within a delivery vehicle into the bloodstream or by intramuscular, subcutaneous, or intraperitoneal means. An appropriate means of delivering HCR monomers to a desired population of cells can be identified by the skilled practitioner based on the particular circumstances without undue experimentation.

HCR Initiators and Initiation of HCR

Target strands of mRNA can serve as initiators of HCR. Embodiments of HCR initiators also include subsequences of mRNA. Based on the disease-associated sequence that is to be targeted, HCR monomers can be designed that only polymerize in the presence of mRNA containing the targeted sequence. If an mRNA subsequence is chosen that is only expressed in certain types of cells e.g. cells with a particular genetic mutation or nucleic acid signature, then HCR will only occur in the targeted cells. Polymerization of HCR monomers will not occur in cells without the target. HCR initiated by the target mRNA sequence creates a large HCR assembly, which can activate PKR. PKR is believed to cause a natural immune response that inhibits protein synthesis and leads to cell death.

Targets contemplated for initiation of HCR are those associated with a disease or disorder, as described in detail above. In some embodiments, the target is a nucleic acid signature or specific mutation in a gene sequence associated with a disease or disorder. Genetic mutations include, but are not limited to, point mutations, non-native genetic fusions, deletion of at least one base, insertion of at least one base, frameshift mutations, and inversions. In other embodiments, the target is a combination of nucleic acid molecules associated with a disease or disorder.

Targets for initiation of HCR also include, but are not limited to, nucleic acid molecules, proteins, peptides, carbohydrates, lipids and small molecules. In some embodiments, the target acts as the initiator for HCR by binding directly to the initiator complement region of an HCR monomer to stimulate HCR polymerization. In other embodiments, the target binds a molecule that is associated with an initiator of HCR polymerization.

Where the disease to be treated is a cancer, an mRNA target is typically one expressed in cancer cells and not in healthy cells or at least to a lesser extent in healthy cells. In some cases, a disease may be identified by the expression of several mRNA targets simultaneously. In this case, the HCR trigger sequence can be designed to initiate HCR only in the event that a specific combination of mRNAs is detected, for example, by detecting a portion of an mRNA fusion entity.

HCR can be performed with RNA monomers instead of, or in conjunction with, DNA monomers. For the basic HCR scheme shown in FIG. 4, RNA hairpins with stems of approximate length 14 and loops of approximate length 4 exhibit similar properties to DNA hairpins with stems of approximate length 18 and loops of approximate length 6. Stems and loops of other lengths are also possible.

Figure 6B:
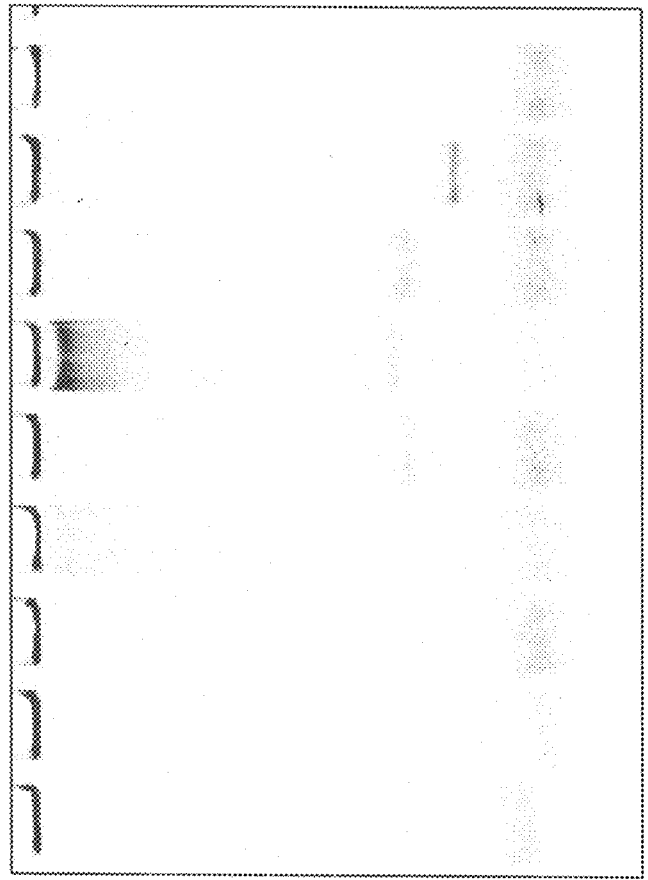
FIG. 6 illustrates the results of RNA-HCR polymer formation studies for (a) Ewing's sarcoma and (b) glioma.

In some embodiments, RNA monomers are used in conjunction with nucleic acid "helper" monomers to facilitate target recognition (FIG. 6). In preferred embodiments, the nucleic acid "helper" monomers are DNA molecules. It has been observed that HCR can be more difficult to initiate using a long mRNA or other nucleic acid target because secondary structure within the mRNA strand reduces accessibility of the target site to the HCR monomers. The use of DNA "helper" monomers that bind to regions flanking the target site helps eliminate competing secondary structures that form between the target site and the flanking regions. HCR is more effectively initiated as a result of the elimination of secondary structure formation within the target mRNA strand. Helper DNA strands can be from about 10 to about 100 bases in length. In some embodiments, the helper DNA strands are from about 10 to about 75 bases in length. In other embodiments, the helper DNA strands are from about 10 to about 50 bases in length. In other embodiments, the helper DNA strands are from about 10 to about 35 bases in length. In preferred embodiments, the helper DNA strands are from about 10 to about 25 bases in length.

In some embodiments, initiation of HCR involving RNA monomers are used in conjunction with a trigger comprising a DNA probe molecule that contains a trigger sequence (FIG. 2). The trigger sequence in the DNA molecule, illustrated as a heavy dashed line in FIG. 2, is exposed upon binding between the DNA molecule and a target mRNA molecule and acts as an initiator to stimulate RNA-HCR polymerization. The single stranded regions on either side of the duplex region of the DNA probe compete with native base pairing within the target molecule to facilitate triggering of the polymerization reaction.

The design of the RNA hairpin monomers can be adjusted such that they bind specifically to nucleic acid targets, mRNA or otherwise. The design can be derived from sequences derived from literature reviews and disclosed in, for example, various databases (e.g. NCBI).

Compositions and Kits for PKR Activation and Therapeutic Benefit

Compositions and kits for recognition of targets associated with a disease or disorder and activation of PKR are contemplated for use within the scope of the subject matter. In preferred embodiments, the compositions comprise a first RNA hairpin monomer and a second RNA hairpin monomer. Upon delivery to a target cell (or sample) and recognition of the target, HCR is initiated causing the first and second hairpin monomers to form long, nicked double stranded RNA polymers that are able to bind and activate one or more PKR molecules for each target that is detected.

The compositions can also contain other components, such as, for example, accessory molecules that facilitate target recognition and aid the formation of HCR polymer products. Accessory molecules typically comprise nucleic acid molecules. In some embodiments, the accessory molecules are DNA helper strands that bind to regions flanking a target nucleic acid sequence. In other embodiments, the accessory molecule is a DNA probe molecule that contains a trigger sequence that initiates HCR upon interaction between the DNA probe molecule and a target.

Furthermore, the composition can comprise a carrier that facilitates the introduction of nucleic acids, such as, for example, RNA hairpin monomers and accessory nucleic acid molecules, into a cell containing a target associated with a disease or disorder. Carriers for delivery of nucleic acids into cells are well known in the art and described above.

A kit for recognition of a target and activation of PKR typically comprises the compositions as described in detail above. In preferred embodiments, the kit is used to deliver HCR hairpin monomers to a population of cells comprising cells comprising a disease-associated target as well as healthy, wild-type cells. In some embodiments, the kit is used to deliver HCR hairpin monomers to the tissues of a patient, wherein the tissues comprise cells comprising a target associated with a disease or disorder. In other embodiments, the kit is used to select for cells containing a target in vitro.

The following examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

EXAMPLES

Example 1

Polymer Formation Studies for Ewing's Sarcoma and Glioma

Polymer formation studies to observe HCR polymerization in the presence and absence of target mRNA were carried out. Stock DNA/RNA solutions were prepared as follows: hairpin 1 ("H1"), hairpin 2 ("H2"), disease-associated target mRNA (either "RNA initiator" comprising only a target sequence without flanking regions or "target mRNA fusion" comprising the target sequence with flanking regions), mRNA 1 ("healthy mRNA 1"), mRNA 2 ("healthy mRNA 2"), and helper DNA ("D1" and "D2" annealed together in one solution). Reactions were set up by combining DNA/RNA components as indicated below. The samples were loaded on 10% TBE-PAGE gels, stained with SYBR gold and imaged on a Fuji fluorescent gel scanner for analysis.

FIG. 6 demonstrates the results of the polymer formation studies for targets from (a) Ewing's sarcoma and (b) glioma. The results demonstrate that RNA-HCR polymerization does not proceed in the absence of the disease-associated target sequence (Lane 3). Polymerization is observed if the target sequence is introduced without flanking regions (Lane 4) but is not observed if a longer mutant mRNA fusion is used that includes flanking regions (Lane 5) due to competing secondary structure that forms in the mRNA. Introduction of DNA helper strands that bind to the flanking regions on either side of the target sequence restores the RNA-HCR polymerization (Lane 6). The two healthy mRNAs that do not contain the fusion do not cause polymerization (Lanes 7 and 8). The helper DNAs also fail to cause poymerization (Lane 9).

The sequences of the DNA/RNA components used for the studies are as follows:

```
Ewing's sarcoma

RNA initiator:
5'-AGCAGAACCCUUCUUAUG-3'                 (SEQ ID NO: 1)

RNA hairpin H1:
5'-CAGACAUAAGAAGGGUUCAGCAGAACCCUU        (SEQ ID NO: 2)
CUUAUG-3'

RNA hairpin H2:
5'-GAACCCUUCUUAUGUCUGCAUAAGAAGGGU        (SEQ ID NO: 3)
UCUGCU-3'

Target mRNA fusion:
5'-CAGAGCAGCAGCUACGGGCAGCAGAACCCU        (SEQ ID NO: 4)
UCUUAUGACUCAGUCAGAAG-3'
(targeted region is underlined with flanking
regions on either side)

Healthy mRNA1:
5'-AUAUAGCCAACAGAGCAGCAGCUACGGGCA        (SEQ ID NO: 5)
GCAGAGUUCAUUCCUUCCGA-3'
(subsequence that is part of targeted region
in the oncogenic fusion is underlined)

Healthy mRNA2:
5'-UGAGUGUCAAAGAAGACCCUUCUUAUGACU        (SEQ ID NO: 6)
CAGUCAGAAGAGGAGCUUGG-3'
(subsequence that is part of targeted region
in the oncogenic fusion is underlined)

Helper DNA D1:
5'-CTTCTGACTGAGT-3'                      (SEQ ID NO: 7)

Helper DNA D2:
5'-GCCCGTAGCTGCTGCTCTG-3'                (SEQ ID NO: 8)

Glioma

RNA initiator:
5'-AAAAGAAAGGUAAUUAUG-3'                 (SEQ ID NO: 9)

RNA hairpin H1:
5'-CAUAAUUACCUUUCUUUUGGGCAAAAGAAA        (SEQ ID NO: 10)
GGUAAU-3'

RNA hairpin H2:
5'-AAAAGAAAGGUAAUUAUGAUUACCUUUCUU        (SEQ ID NO: 11)
UUGCCC-3'

Target mRNA fusion:
5'-AGUCGGGCUCUGGAGGAAAAGAAAGGUAAU        (SEQ ID NO: 12)
UAUGUGGUGACAGAUCACGG-3'
(targeted region is underlined with flanking
regions on either side)
```

-continued

Healthy mRNA1:
5'-CUGCCCGGCGAGUCGGGCUCUGGAGG<u>AAAA</u>   (SEQ ID NO: 13)
<u>GAAA</u>GUUUGCCAAGGCACGA-3'
(subsequence that is part of targeted region
in the oncogenic fusion is underlined)

Healthy mRNA2:
5'-UGAAGAAGUGUCCCC<u>GUAAUUAU</u>GUGGUGA   (SEQ ID NO: 14)
CAGAUCACGGCUCGUGCGUC-3'
(subsequence that is part of targeted region
in the oncogenic fusion is underlined)

Helper DNA D1:
5'-CCGTGATCTGTCACCA-3'          (SEQ ID NO: 15)

Helper DNA D2:
5'-CCTCCAGAGCCCGACT-3'          (SEQ ID NO: 16)

Example 2

PKR Activation Studies for Ewing's Sarcoma and Glioma

PKR activation studies in the presence and absence of disease-associated target mRNA were carried out. PKR protein was prepared as described in Zheng and Bevilacqua (Zheng, X. and P. C. Bevilacqua. *RNA* 10:1934-1945 (2004), herein incorporated by reference in its entirety). Protocols for PKR activation studies were based on Matsui, T. et al. (Matsui, T. et al. *Biochem Biophys Res Comm* 284:798-807 (2001), herein incorporated by reference in its entirety). Stock DNA/RNA solutions were prepared as follows: hairpin 1 ("H1"), hairpin 2 ("H2"), disease-associated target mRNA ("target mRNA fusion" comprising a target sequence with flanking regions), mRNA 1 ("healthy mRNA 1"), mRNA 2 ("health mRNA 2"), and helper DNA ("D1" and "D2" annealed together in one solution). A comparison antisense solution based on the protocol of Shir and Levitzki (Shir, A., and A. Levitzski. *Nature Biotechnology* 20:895-900 (2002), herein incorporated by reference in its entirety) was also prepared. Reactions were set up by combining the components as indicated below. The reactions were carried out using radioactive ATP solution and phosphatased PKR. Samples were then loaded onto prepared 10% SDS-PAGE gel and analyzed according to standard protein gel and radioactive visualization protocols.

FIG. 7 illustrates the results of the PKR activation study for (a) Ewing's sarcoma and (b) glioma. The results show that RNA-HCR causes a strong activation of PKR in the presence of the target mRNA fusion (Lane 3), but is not active in the absence of the target (Lane 2) or in the presence of either healthy mRNA1 (Lane 4) or healthy mRNA 2 (Lane 5). The method of Shir and Levitzki is demonstrated in Lanes 6-9. PKR activation in the presence of the target mRNA fusion (Lane 7) is not as strong as using RNA-HCR (Lane 3). Also, the off states in the presence of either healthy mRNA1 (Lane 8) or healthy mRNA2 (Lane 9) are not as good as those observed using RNA-HCR (Lanes 4 and 5). As a result, RNA-HCR also provides a better on/off ratio for activation of PKR.

Lanes 10 and 11 show that PKR activation using RNA-HCR depends on the use of both hairpin species as expected.

Example 3

In Vivo HCR-RNA Activation of Protein Kinase PKR

HCR hairpins are delivered to target cells using standard gene delivery methods. In the presence of an intracellular mRNA target, HCR polymerization is initiated. The products act as PKR binding domains to activate PKR. Activation of PKR leads to inhibition of translation and cell apoptosis in diseased cells containing the intracellular target.

Example 4

In Vivo RNA-HCR Therapy of Diseases Caused by Fused Gene Mutations

Two or more genes are fused together to encode an oncogenic protein (Dohjima, T. et al. *Molecular Therapy* 7: 811-816 (2003), herein incorporated by reference in its entirety). Although the two or more genes are present in healthy cells, the overlap region between the genes is a distinct signature found only in tumor cells. HCR-RNA hairpin monomers are designed to polymerize in the presence of a target sequence included within the overlap region. The monomers have stems ranging in length between 10 and 35 base pairs. The hairpin monomers are introduced in vivo into tumor cells by gene delivery methods known in the art. Recognition of the target overlap region by the HCR-RNA monomers initiates hybridization chain reaction, which produces long nicked RNA duplexes in the tumor cells. This HCR product activates PKR in the tumor cells, which slows the production of all the proteins in the tumor cells. The activation of PKR also induces apoptosis. The triggering of this response slows and can reverse the growth of the tumor.

Example 5

HCR-Aptamer Therapy of Disease

An aptamer is identified that is able to specifically bind a target molecule within a diseased cell. HCR-RNA hairpin monomers are designed that link the aptamer to a first RNA hairpin monomer in such a way that in the absence of the target, the aptamer does not allow opening of the hairpin monomer and does not initiate HCR. The HCR-RNA hairpin monomers are introduced in vivo into cells by gene delivery methods known in the art. Recognition between the aptamer on a first RNA hairpin monomer and the target allows opening of the first monomer, initiating polymerization by HCR and producing long nicked double-stranded RNA in the target cells. The HCR product activates PKR in the target cells, which slows the production of all the proteins within the cells and induces apoptosis. The triggering of this response slows and can reverse the growth of the diseased cells or kills the diseased cells.

What is claimed is:

1. A method of activating the RNA-dependent protein kinase PKR by hybridization chain reaction (HCR), the method comprising:
A method of activating the RNA-dependent protein kinase PKR by hybridization chain reaction (HCR), the method comprising:
   providing cells that comprise PKR and an initiator, wherein the initiator comprises a nucleic acid initiation region and first complementary region;
   contacting said cells with a first RNA hairpin monomer comprising:
      i) a first duplex region comprising second and third complementary stem regiong, wherein the second complementary region is substanstially complementary to the first complementary region of the initiator,
      ii) a first hairpin loop region at an end of the first duplen region, and
      iii) an initiator complement region that comprises a sticky end and that is substantially complementary to the initiation region of the initiator; contacting said cells with a second RNA hairpin monomer comprising:
      i) a second duplex region comprising fourth and fifth complementary stem regions,
      ii) a second sticky end region that is substantially complementary to the first hairpin loop region to the first monomer, and
      iii) a second hairpin loop region that is substantially complementary to the sticky end of the initiator complement region of the first monomer;
   wherein the first and second monomers hybridize in a chain reaction upon binding of the initiator to the first monomer, thereby forming a double-stranded RNA polymer that at least comprises the first and second monomers and that activates PKR.

2. The method of claim 1, wherein the polymer comprises at least 35 base pairs.

3. The method of claim 1, wherein the initiator is a portion of a target nucleic acid.

4. The method of claim 3, further comprising: contacting the cells with at least one accessory molecule comprising a DNA sequence that binds to a region of the initiator.

5. The method of claim 1, wherein the initiator is able to bind to the initiator complement region when a target is present in the cells.

6. The method of claim 5, wherein the target is associated with a disease or disorder.

7. The method of claim 6, wherein the target is an mRNA associated with a cancer.

8. The method of claim 6, wherein the target is a viral nucleic acid.

9. The method of claim 1, wherein the initiator is part of a nucleic acid probe.

10. The method of claim 9, wherein upon binding of the nucleic acid probe to a target nucleic acid sequence the initiator is made available to bind to the initiator complement region of the first monomer.

11. The method of claim 10, wherein the target is an mRNA molecule associated with a disease or disorder.

12. The method of claim 5, wherein the initiator comprises a recognition molecule comprising a nucleic acid such that upon binding of the recognition molecule to the target the initiator is made available to bind to the initiator complement region of the first monomer.

13. The method of claim 12, wherein the recognition molecule is an aptamer.

14. The method of claim 12, wherein the target is a nucleic acid.

15. The method of claim 12, wherein the target is selected from the group consisting of polypeptides, carbohydrates, lipids and small molecules.

16. A method of activiating PKR by hybridization chain reaction (HCR) in a cell that comprises PKR and an initiator, wherein the initiator comprises a nucleic acid initiation region and first complementary region, the method comprising;
  contacting said cell with a first RNA hairpin monomer comprising:
    i) a first duplex region comprising second and third complementary segments, wherein the second complementary segment is substantially complementary to the first complementary region of the initiator,
    ii) a loop segment at an end of the first duplex region, and
    iii) a first sticky end that is substantially complementary to the initiation region of the initiator;
  contacting said cell with a second RNA hairpin monomer comprising:
    i) a propagation region that is substantially complementary to a portion of the first monomer, and
    ii) a second sticky end that is substantially complementary to a portion of the first hairpin loop region of the first monomer,
  wherein the first and second hairpin monomers hybridize in a chain reaction upon binding of the initiator to the first monomer, thereby forming a double-stranded RNA polymer that activates PKR.

17. A method of activating the RNA-dependent protein kinase PKR by hybridization chain reaction (HCR), the method comprising:
A method of activating the RNA-dependent protein kinase PKR by hybridization chain reaction (HCR), the method comprising:
  providing a sample that comprises PKR and an initiator, wherein the initiator comprises a nucleic acid initiation region and first complementary region;
  contacting said sample with a first RNA hairpin monomer comprising:
    i) a first duplex region comprising second and third complementary stem regions, wherein the second complementary region is substantially complementary to the first complementary region of the initiator,
    ii) a first hairpin loop region at an end of the first duplex region, and
    iii) an initiator complement region that comprises a sticky end and that is substantially complementary to the initiation region of the initiator;
  contacting said sample with a second RNA hairpin monomer comprising:
    i) a second duplex region comprising fourth and fifth complementary stem regions,
    ii) a second sticky end region that is substantially complementary to the first hairpin loop region of the first monomer, and
    iii) a second hairpin loop region that is substantially complementary to the sticky end of the initiator complement region of the first monomer;
  wherein the first and second monomers hybridize in a chain reaction upon binding of the initiator to the first monomer thereby forming a double-stranded RNA polymer, wherein the double-stranded RNA polymer comprising at least the first and second RNA monomers activates PKR.

18. The method of claim 17, wherein the polymer comprises at least 35 base pairs.

19. The method of claim 17, wherein the initiator is a portion of a target nucleic acid.

20. The method of claim 19, further comprising: contacting the sample with at least one accessory molecule comprising a DNA sequence that binds to a region of the initiator.

21. The method of claim 17, wherein the initiator is able to bind to the initiator complement region when a target is present in the sample.

22. The method of claim 21, wherein the target is associated with a disease or disorder.

23. The method of claim 22, wherein the target is an mRNA associated with a cancer.

24. The method of claim 22, wherein the target is a viral nucleic acid.

25. The method of claim 17, wherein the initiator is part of a nucleic acid probe.

26. The method of claim 25, wherein upon binding of the nucleic acid probe to a target nucleic acid sequence the initiator is made available to bind to the initiator complement region of the first monomer.

27. The method of claim 26, wherein the target is an mRNA molecule associated with a disease or disorder.

28. The method of claim 21, wherein the initiator comprises a recognition molecule comprising a nucleic acid such that upon binding of the recognition molecule to the target the initiator is made available to bind to the initiator complement region of the first monomer.

29. The method of claim 28, wherein the recognition molecule is an aptamer.

30. The method of claim 28, wherein the target is a nucleic acid.

31. The method of claim 28, wherein the target is selected from the group consisting of polypeptides, carbohydrates, lipids and small molecules.

32. A method of activating RNA-dependent protein kinase PKR to treat a disease by specifically targeting a diseased cell comprising PKR and an initiator by hybridization chain reaction (HCR) to induce cell death, the method comprising:
  contacting said cell with a first RNA hairpin monomer, wherein the initiator comprises:
  a nucleic acid initiation region and a first complementary region,
  and wherein the first RNA hairpin monomer comprises:
    i) a first duplex region comprising second and third complementary stem regions, wherein the second complementary region is substantially complementary to the first complementary region of the initiator,
    ii) a first hairpin loop region at an end of the first duplex region, and
    iii) an initiator complement region that comprises a sticky end and that is substantially complementary to the initiation region of the initiator;
  and contacting said cell with a second RNA hairpin monomer comprising:
    i) a second duplex region comprising fourth and fifth complementary stem regions,
    ii) a second sticky end region that is substantially complementary to the first hairpin loop region of the first monomer, and
    iii) a second hairpin loop region that is substantially complementary to the sticky end of the initiator complement region of the first monomer;
  wherein the first and second monomers hybridize in a chain reaction upon binding of the initiator to the first monomer, thereby forming a double-stranded RNA polymer comprising at least the first and second monomers, wherein binding of the initiator to the initiator complement region occurs specifically in the diseased cell, wherein the double-stranded RNA polymer activates PKR in said cell, and wherein the RNA hairpin monomer will not activate PKR by itself.

33. The method of claim 1, wherein the first RNA hairpin monomer comprises an analog RNA nucleotide.

34. The method of claim 1, wherein the second RNA hairpin monomer comprises an analog RNA nucleotide.

* * * * *

UNITED STATES PATENT AND TRADEMARK OFFICE
CERTIFICATE OF CORRECTION

PATENT NO. : 7,960,357 B2
APPLICATION NO. : 11/544306
DATED : June 14, 2011
INVENTOR(S) : Dirks et al.

It is certified that error appears in the above-identified patent and that said Letters Patent is hereby corrected as shown below:

At column 6, line 33, please remove "vif; nef" and insert therefore, --vif, nef,--.

At column 9, line 5, please remove "calorimetric" and insert therefore, --colorimetric--.

At column 18, lines 39-41, in Claim 1, after "comprising:" please remove "A method of activating the RNA-dependent protein kinase PKR by hybridization chain reaction (HCR), the method comprising:".

At column 25, approximately line 48, in Claim 1, please remove "regiong," and insert therefore, --regions,--.

At column 25, approximately line 49, in Claim 1, please remove "substanstially" and insert therefore, --substantially--.

At column 25, approximately line 54, in Claim 1, please remove "duplen" and insert therefore, --duplex--.

At column 25, line 63, in Claim 1, please remove "region to" and insert therefore, --region of--.

At column 27, lines 36-38, in Claim 17, after "comprising:" please remove "A method of activating the RNA-dependent protein kinase PKR by hybridization chain reaction (HCR), the method comprising:".

Signed and Sealed this
Twenty-ninth Day of November, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,960,357 B2 | Page 1 of 1 |
| APPLICATION NO. | : 11/544306 | |
| DATED | : June 14, 2011 | |
| INVENTOR(S) | : Robert Dirks et al. | |

It is certified that error appears in the above-identified patent and that said Letters Patent is hereby corrected as shown below:

Column 1, Line 11, before the heading "BACKGROUND OF THE INVENTION", please add

-- STATEMENT REGARDING FEDERALLY SPONSORED R&D

This invention was made with government support under Grant No. CA140759 awarded by the National Institutes of Health. The government has certain rights in the invention. --.

Signed and Sealed this
Twenty-fourth Day of November, 2015

Michelle K. Lee
*Director of the United States Patent and Trademark Office*